United States Patent
Saleem

(10) Patent No.: US 10,247,718 B2
(45) Date of Patent: *Apr. 2, 2019

(54) NON-DESTRUCTIVE APPARATUS, SYSTEM AND METHOD FOR DETERMINING PULL-OUT CAPACITY OF ANCHOR BOLTS

(71) Applicant: University of Dammam, Dammam (SA)

(72) Inventor: Muhammad Saleem, Dammam (SA)

(73) Assignee: University of Dammam, Dammam (SA)

( * ) Notice: Subject to any disclaimer, the term of this patent is extended or adjusted under 35 U.S.C. 154(b) by 409 days.

This patent is subject to a terminal disclaimer.

(21) Appl. No.: 14/880,185

(22) Filed: Oct. 9, 2015

(65) Prior Publication Data
US 2017/0102304 A1  Apr. 13, 2017

(51) Int. Cl.
*G01N 3/34* (2006.01)
*G01N 33/38* (2006.01)
(Continued)

(52) U.S. Cl.
CPC ........ *G01N 33/383* (2013.01); *G01M 99/007* (2013.01); *G01N 29/00* (2013.01);
(Continued)

(58) Field of Classification Search
CPC ........ G01M 99/007; G01N 2203/0039; G01N 2203/0083; G01N 29/00; G01N 33/383
See application file for complete search history.

(56) References Cited

U.S. PATENT DOCUMENTS 4,062,229 A * 12/1977 Godfrey ................. G01H 13/00
                                                            73/582
4,103,540 A *  8/1978 McLaughlin ............ G01N 3/00
                                                            73/803
(Continued)

FOREIGN PATENT DOCUMENTS

CN      1793897 A       6/2006
JP    56-154642 A      11/1981
(Continued)

OTHER PUBLICATIONS

Priyantha W. Jayawickrama, et al., "Non-Destructive Evaluation of Installed Soil Nails", Multidisciplinary Research in Transportation, Dec. 2007, 260 pages.

*Primary Examiner* — Freddie Kirkland, III
(74) *Attorney, Agent, or Firm* — Oblon, McClelland, Maier & Neustadt, L.L.P.

(57) ABSTRACT

Embodiments include an apparatus for determining a pull-out capacity of a bolt disposed in concrete. The apparatus includes control processing circuitry and a Schmidt hammer electrically connected to the control processing circuitry. The Schmidt hammer is configured to strike the bolt during a test event and to record a rebound value for the bolt. The control processing circuitry is configured to calculate an estimated pull-out strength for the bolt using the rebound value of the bolt that resulted from the test event, a predetermined bolt diameter, a predetermined bolt embedment length in the concrete, and an estimated predetermined strength of concrete. The apparatus also includes a remote computer configured to communicate with the control processing circuitry and to store an estimated pull-out strength of the bolt. The control processing circuitry includes a memory and a database.

18 Claims, 32 Drawing Sheets

(51) Int. Cl.
*G01N 29/00* (2006.01)
*G01M 99/00* (2011.01)

(52) U.S. Cl.
CPC ........... *G01N 2203/0039* (2013.01); *G01N 2203/0083* (2013.01)

(56) References Cited

U.S. PATENT DOCUMENTS

| | | | | |
|---|---|---|---|---|
| 4,198,865 | A * | 4/1980 | Tarpley, Jr. | G01N 3/32 73/582 |
| 5,798,981 | A * | 8/1998 | Littlejohn | G01N 29/045 367/13 |
| 7,043,989 | B2 * | 5/2006 | Brink | E21D 20/02 73/579 |
| 7,555,931 | B2 * | 7/2009 | Palmer | C21C 5/441 73/12.09 |
| 9,524,634 | B2 * | 12/2016 | Tillotson | H04Q 9/00 |
| 9,618,436 | B2 * | 4/2017 | Boitnott | G01N 3/40 |
| 9,726,657 | B2 * | 8/2017 | Saleem | G01N 33/383 |
| 2012/0174525 | A1 * | 7/2012 | Hinshaw | B25F 5/00 52/741.1 |
| 2017/0102300 | A1 * | 4/2017 | Saleem | G01M 99/00 |

FOREIGN PATENT DOCUMENTS

| | | |
|---|---|---|
| JP | 2008-65708 A | 3/2008 |
| JP | 2015-45637 A | 3/2015 |

\* cited by examiner

NON-DESTRUCTIVE APPARATUS, SYSTEM AND METHOD FOR DETERMINING PULL-OUT CAPACITY OF ANCHOR BOLTS

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Concrete anchors are extensively used in the construction industry. Their applications range from erecting permanent objects such as sign poles, direction signs, lighting poles etc., to temporary support structures. Several destructive testing equipment exist in the market which can be used to evaluate the load carrying capacity of concrete anchors. However, as recognized by the present inventor no non-destructive testing method has been proposed which can give estimation about their load carrying capacity.

Specifically, anchor bolts are excessively used in the construction industry these days. Applications range from using these bolts for installation of permanent fixtures such as sign boards, light posts to smaller temporary fixes such as installation of shuttering and netting, etc.

In construction technology, pull-out testing generally establishes the holding force of anchors and fixings in most construction materials, such as concrete. In conventional pull-out testing of anchor bolts/bars require applying a specific tensile load to an anchor bolt/bar in order that the anchor bolt/bar can sustain such a test condition for a period of time. Deformation of the anchor tested can also be measured to understand the relationship between force and displacement during testing.

Nondestructive testing or non-destructive testing (NDT) is a wide group of analysis techniques used in science and industry to evaluate the properties of a material, component or system without causing damage.

Concrete anchors are used in construction industry for a variety of objectives. These objectives range from installing permanent objects to temporary quick fix solutions. Concrete anchors come in various sizes and shapes. The selection of a suitable anchor for a particular job depends on a variety of factors such as material for installation, required load carrying capacity, nature of job, environmental conditions, and availability of skilled labor. For large capacity anchors, pre-construction installation is preferred, however for the majority of cases post-construction installation is suitable.

Further, the time, effort, cost, and equipment needed to conduct conventional pull-out testing can be extensive and tedious, requiring skilled labor, a linear variable displacement transducer (LVDT), a data acquisition system, and hydraulic pumps with pressure gauges. Conventional material testing and quality assurance may play a pivotal role in every major construction project. Currently, for large scale projects an on-site material testing and quality assurance lab may be established. Hence, quick, reliable and effective methods and apparatuses are preferred to achieve the quantitative analysis of material strength fixed to ground.

SUMMARY

Embodiments include an apparatus for determining a pull-out capacity of a bolt disposed in concrete. The apparatus includes control processing circuitry and a Schmidt hammer electrically connected to the control processing circuitry. The Schmidt hammer is configured to strike the bolt during a test event and to record a rebound value for the bolt. The control processing circuitry is configured to calculate an estimated pull-out strength for the bolt using the rebound value of the bolt that resulted from the test event, a predetermined bolt diameter, a predetermined bolt embedment length in the concrete, and an estimated predetermined strength of concrete.

Embodiments also include a non-destructive method for determining a pull-out capacity of a bolt disposed in concrete. The method includes impacting a Schmidt hammer on the bolt. The method also includes recording in a computer memory a hammer rebound value from the Schmidt hammer. The method further includes comparing with circuitry the recorded rebound value with a stored value that is an association of the hammer rebound value to pull-out strength so as to estimate a pull-out load carrying capacity of the bolt.

Embodiments further include a system for determining a pull-out capacity of a bolt disposed in concrete. The system includes control processing circuitry. The system also includes a Schmidt hammer electrically connected to the control processing circuitry. The Schmidt hammer is configured to strike the bolt during a test event and to record a rebound value for the bolt. The system further includes a remote computer configured to communicate with the control processing circuitry and to store an estimated pull-out strength of the bolt. The control processing circuitry includes a memory and a database. The system also includes a global positioning system (GPS) receiver configured to triangulate from wireless transmissions a plurality of location transmitters a location of the bolt that is being installed in which the remote computer stores the location, with a bolt ID, and associates the bolt ID and location with the rebound value and the estimated pull-out strength. The control processing circuitry is configured to calculate the estimated pull-out strength for the bolt using the rebound value of the bolt that resulted from the test event, a predetermined bolt diameter, a predetermined bolt embedment length in the concrete, and an estimated predetermined strength of concrete.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Currently there exists several commercially available devices which can be used to evaluate the loading capacity of concrete anchors, however all of them rely on destructive testing. The present disclosure develops a non-destructive method for load capacity evaluation by relating a pull-out strength of concrete anchors to a rebound value of Schmidt hammer, which traditionally is used to measure the compressive strength of concrete. The Schmidt hammer was developed in 1948 by a Swiss engineer Ernst Schmidt and is a portable, cost-effective instrument capable of estimating the elastic properties of hardened concrete. The Schmidt hammer is a practical non-destructive method that has been used worldwide as an index test estimating the compressive strength of concrete.

Figure 1:
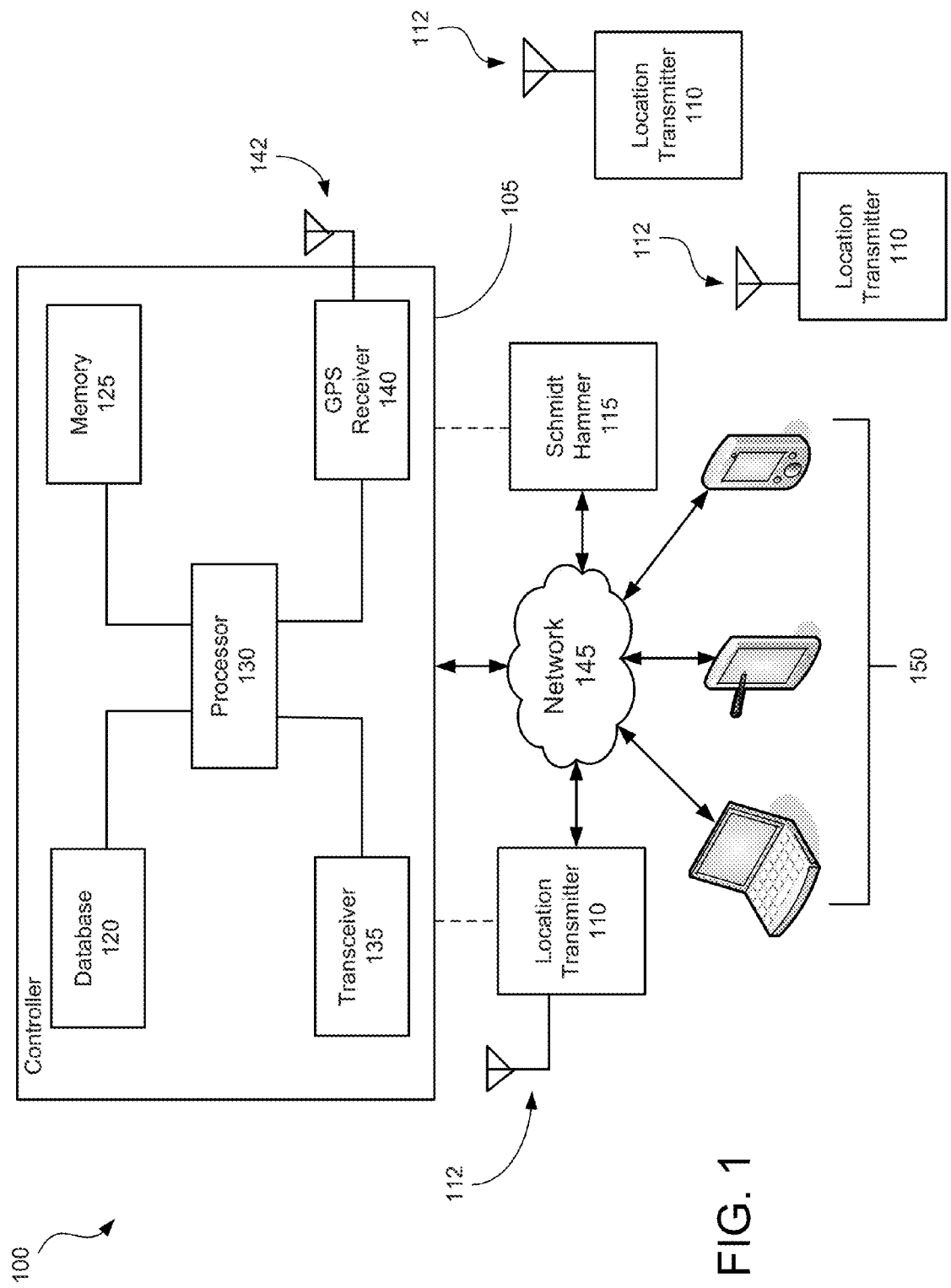
FIG. 1 is a block diagram of a non-destructive apparatus and system for determining pull-out capacity of anchor bolts according to certain embodiments of the disclosure.

Referring now to the drawings, wherein like reference numerals designate identical or corresponding parts throughout the several views, FIG. 1 is a block diagram of a non-destructive apparatus and system 100 for determining pull-out capacity of anchor bolts according to certain embodiments of the disclosure. In FIG. 1, apparatus and system 100 may include a controller 105, location transmitters 110, a Schmidt Hammer apparatus 115, and a network 145.

Controller 105 may include a database 120, a memory 125, a processor 130, a transceiver 135, and a GPS receiver 140. In some embodiments, database 120 may include a plurality of databases, memory 125 may include a plurality of memories, processor 130 may include a plurality of processors, transceiver 135 may include a plurality of transceivers, and GPS receiver 140 may include a plurality of GPS receivers. Controller 105 may be connected to network 145 via Ethernet, WiFi, cellular, and Internet or the like.

Processor 130 may be configured to compare data received from Schmidt hammer apparatus 115, such as rebound value, R to data stored in database 120, such as embedment length, anchor bolt diameter, anchor bolt vertical alignment with respect to a concrete base (i.e., perpendicular to the concrete base), and strength of the concrete, each as predetermined values or data.

Network 145 may be connected via Ethernet, WiFi, cellular, Internet or the like to a remote computer 150, such as a laptop computer, a tablet computer, and/or a smartphone, or the like.

In certain embodiments, remote computer 150 may be configured to monitor an installation process in real time of each anchor bolt and provide feedback to an installer whether a particular installed anchor has the required pull-out load carrying capacity.

In some embodiments remote computer 150 may be configured to monitor an installation process in real time of each anchor bolt and provide a certification report for all the anchor bolts installed on a particular job so corrective action may be taken later on the anchors that were installed incorrectly.

Location transmitters 110 may include a plurality of location transmitters connected to network 145 via WiFi, cellular, or the like and/or electrically connected to controller 105 directly. Schmidt hammer apparatus 115 may include a plurality of Schmidt hammer apparatuses connected to network 145 via Ethernet, WiFi, cellular, Internet and/or the like or electrically connected to controller 105 directly.

Location transmitters 110 are disposed at three distinct distances about an installation site, each transmitting beacon signals to the Schmidt hammer 115. The Schmidt hammer 115 records a particular location of the anchor bolt being tested by using triangulation and a GPS coordinate from the GPS receiver 140. Thus, each tested anchor bolt is assigned a unique ID, that is saved in association with particular locations and a Schmidt hammer rebound value, R.

Moreover, anchor bolts are assigned an identifier anchor ID for each anchor bolt and transmitted to controller 105 via network 145. Further, the processor 130 may be configured to perform a triangulation calculation in the Schmidt hammer 115 based on the transmissions to geo-locate the anchor bolts. Alternatively, the controller 105 may be a separate device than the Schmidt hammer 115 and may perform the triangulation calculations on behalf of the Schmidt hammer 115 based on the data collected by the Schmidt hammer 115. Location transmitters 110 may include triangulation antennas 112 incorporated therein. For this example, in order to perform the triangulation calculation a combination of at least three location transmitters 110 (base stations) may be used.

For example, in some embodiments, controller 105 includes triangulation antennas 112 connected to a plurality of location transmitters 110 to accurately locate a particular anchor bolt that is being installed in which the remote computer 150 stores the location, with an anchor ID, and associates the anchor ID and location with the Schmidt hammer measurement estimated pull-out load carrying capacity, P.

Schmidt hammer apparatus 115 may be disposed proximal each anchor bolt for determining and transmitting a Schmidt hammer rebound value, R for each anchor bolt to controller 105 via network 145. In some embodiments, Schmidt hammer apparatus 115 may include or be electrically connected to transceiver 135 to provide a wireless communications capability.

Database 120 may include stored rebound values, R, correlated with stored pull-out strengths of similar anchors based on anchor diameter, anchor embedment length, concrete strength, and anchor alignment. Transceiver 135 may include a cellular transmitter and receiver configured to communicate with network 145, Location transmitters 110, and/or Schmidt hammer apparatus 115.

Figure 2:
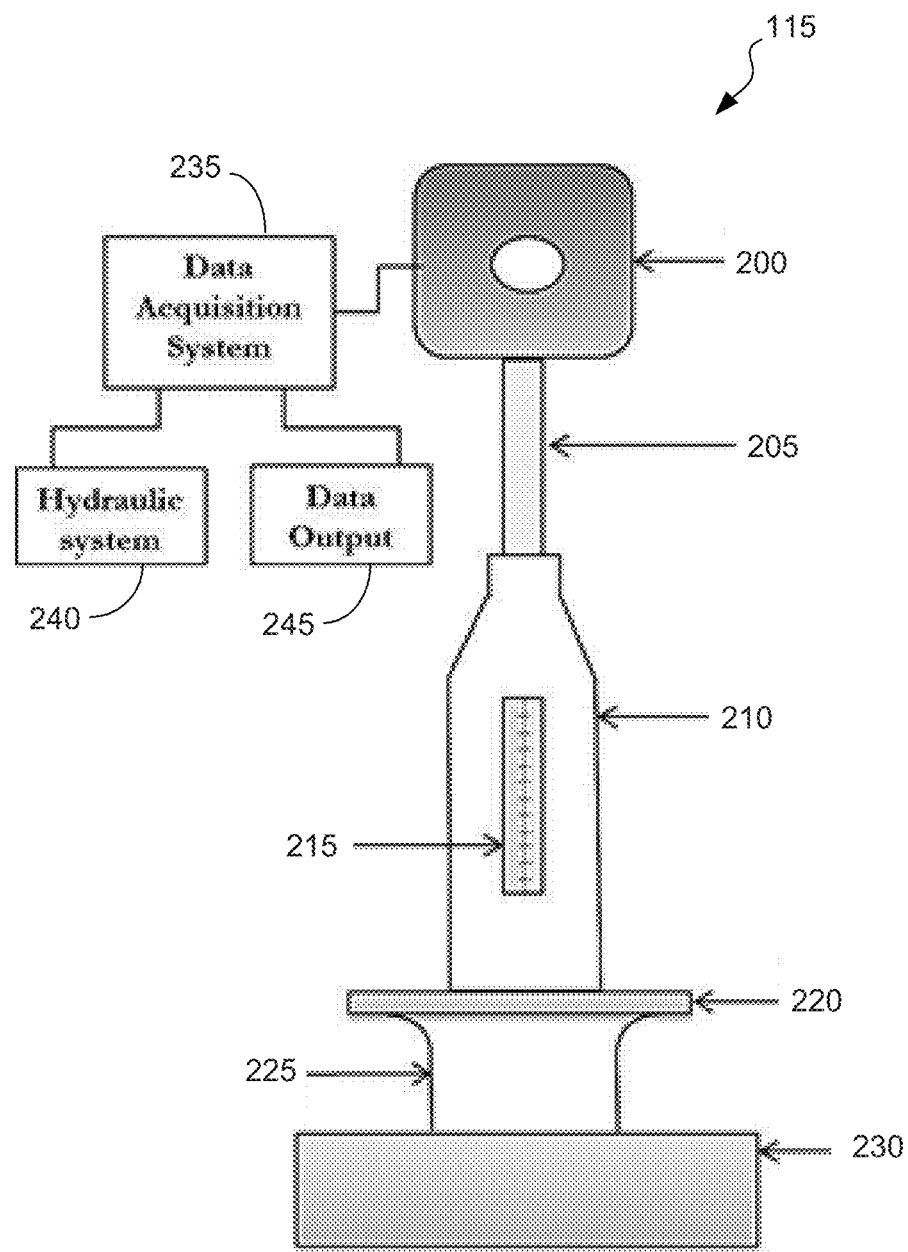
FIG. 2 is a schematic diagram of a Schmidt Hammer apparatus according to certain embodiments of the disclosure.

FIG. 2 is a schematic diagram of a Schmidt hammer apparatus 115 according to certain embodiments of the disclosure. In FIG. 2, apparatus 115 may include a load cell 200, a plunger 205, a Schmidt hammer 210, a rebound number indicator 215, a bearing plate 220, a moveable base 225, and a hydraulic assembly 230. Apparatus 115 may also include a digital data acquisition system 235, a hydraulic system 240 and a data output device 245.

In FIG. 2, the Schmidt hammer apparatus 115 may be used to measure the rebound number, R via indicator 215 and impact load via load cell 200 imparted by the Schmidt hammer 210. In operation, the base of the hammer 210 may be fixed and the plunger 205 may be lowered gradually, finally the impact load may be recorded by the digital data acquisition system 235.

Data output device 245 may be electrically connected to data acquisition system 235 and to controller 105 and/or connected to network 145 via Ethernet, WiFi, cellular, and Internet or the like.

Schmidt hammer apparatus 115 may be configured to determine an impact load on anchor bolts. Anchor bolts used in the construction industry are subjected to a variety of loadings during their life cycle. During the life cycle these bolts are subjected to a variety of environmental and physical loadings. Loadings vary from monotonic loading to cyclic loading to impact loading. Much research in the past has been focused on the effect of monotonic and cyclic loading. The present disclosure discusses the effect of impact loading on the load-carrying capacity of anchor bolts, for example, 8 millimeter (mm), 10 mm, and 12 mm diameter bolts with constant embedment length and concrete strength were subjected to impact loading. The impact loading is such that is generated using a Schmidt hammer apparatus 115, for example, a Concrete Rebound Schmidt Hammer. Concrete quality, anchor alignment, anchor diameter, and water ingress were taken into consideration. An analytical model is also disclosed which takes into consideration the interfacial bonding between the bolt and surrounding concrete matrix, bolt geometric shape, diameter, alignment and embedment length. Pull-out deformational response comparison between the analytical model and experimental results reveals that the model is successfully able to depict the maximum load carrying capacity and the pull-out mechanism as per experimental investigation. From the analysis and presented results it is evident that the bond performance of the bolts, bolts embedded in poor quality concrete, water ingress and hidden defects can be identified by imparting the impact energy.

Further, work in the past has been focused on evaluating the deformational response of anchor bolts subjected to either monotonic or cyclic loading with little attention on the effects of impact loading. In this regard, the present disclosure discusses the effects of impact loading on the deformational response of anchor bolts and aims to evaluate the bond performance of pre-construction installed anchor bolts subjected to impact loading. The factors affecting the anchor bolt pull-out strength such as inherent defects in surrounding concrete, embedment length, anchor bolt diameter, its alignment and water ingress are taken into consideration. Three diameter anchor bolts are used for example, 8 mm, 10 mm, and 12 mm. A computer-based analytical circuitry capable of successfully predicting the pull-out deformational response is also presented. From the experimentation it has been deduced that quality of bond plays a crucial role in overall load carrying capacity, P and bolts with poor bond depict lower rebound number, R while bolts with good bond result in a higher rebound number, R.

Embodiments of the present disclosure explain a relationship between the pull-out load carrying capacity, P, of concrete anchors and the Schmidt hammer rebound value, R. In some embodiments, the load carrying capacity of the concrete anchors depends on anchor embedment length, anchor diameter, concrete strength, and anchor alignment. The effect of anchor alignment on load carrying capacity shows that anchors with misalignment of more than 5% from vertical can lead to lower load carrying capacity. In addition, it is also possible to identify the misaligned concrete anchor, anchor bolt installed in poor quality concrete using the test data comparisons.

Figure 14A:
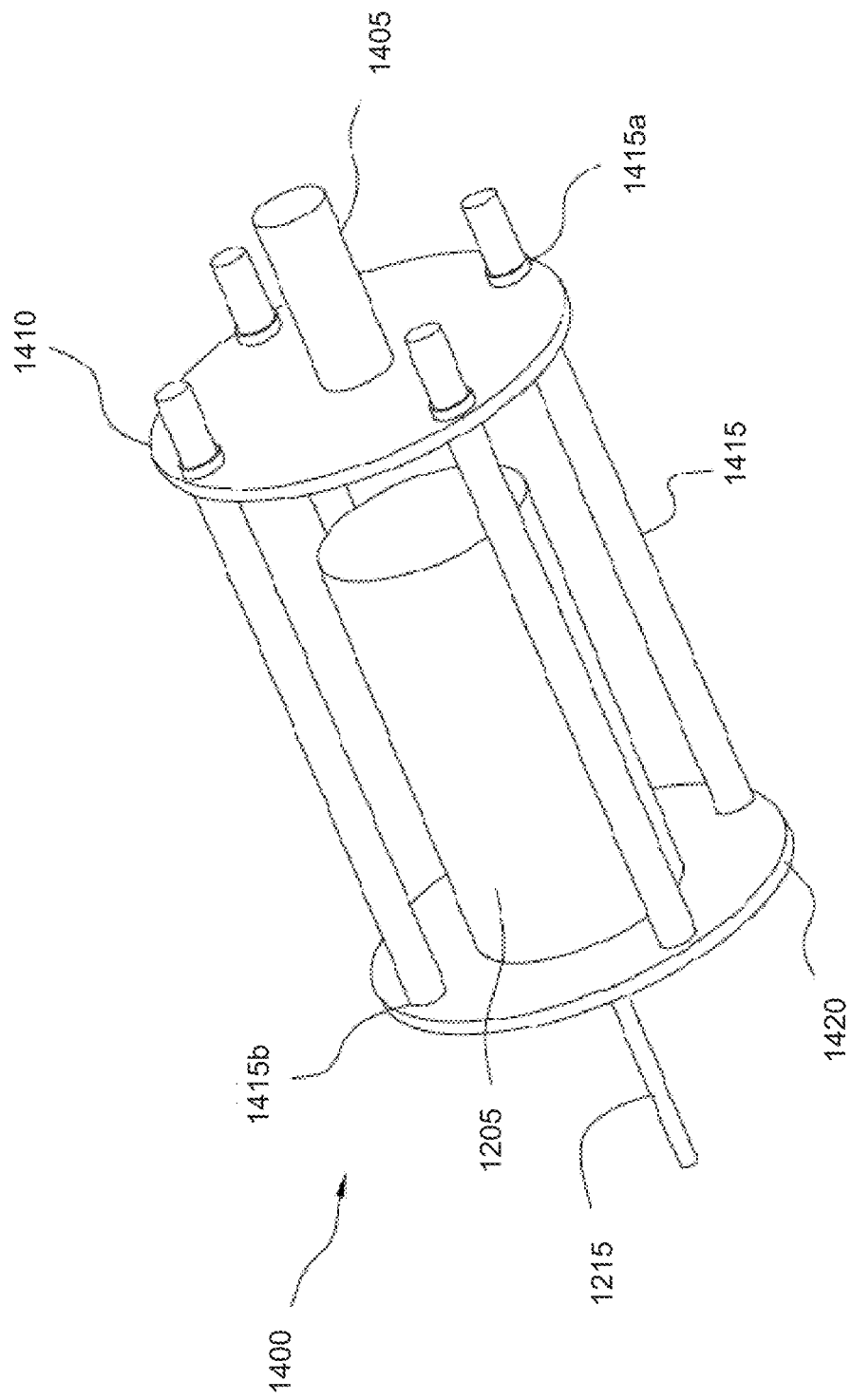
FIG. 14A is a schematic perspective view of an anchor cage assembly including a concrete sample according to certain embodiments of the disclosure.
Figure 15A:
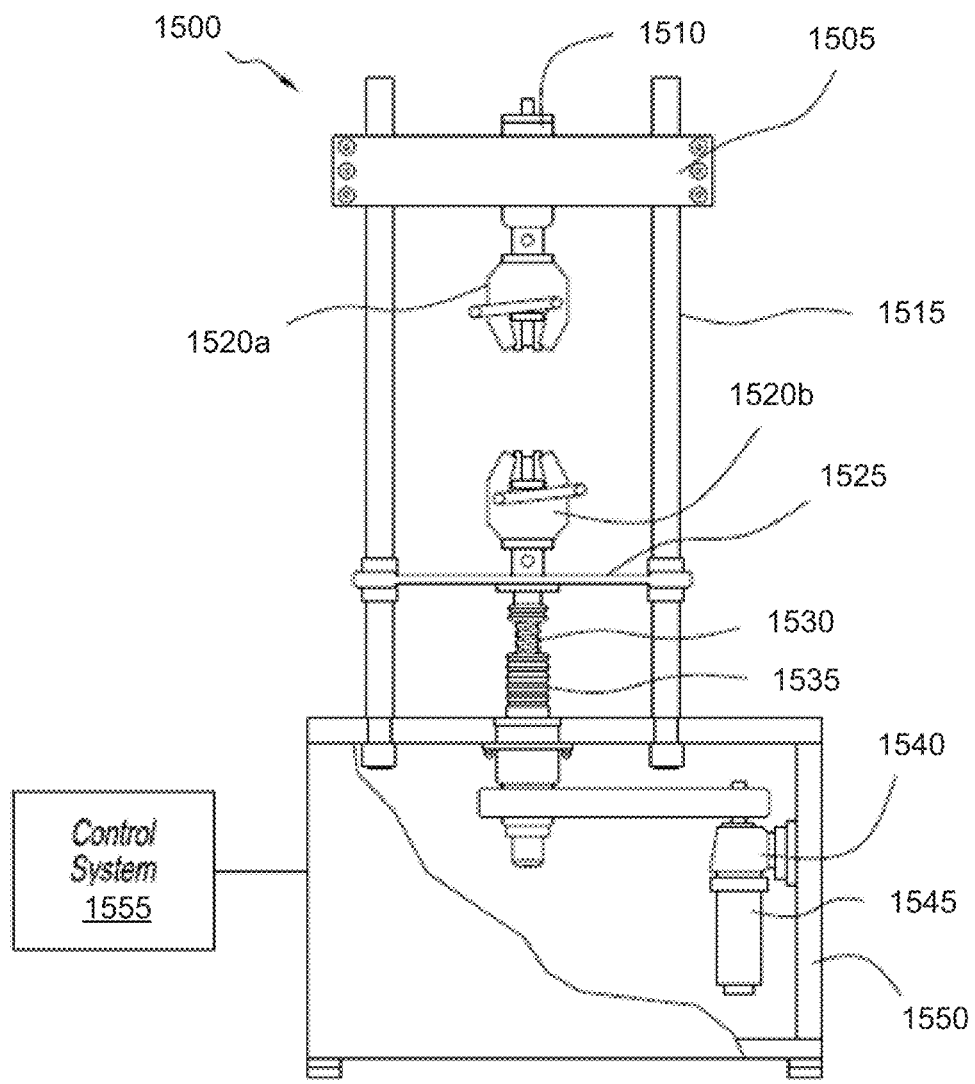
FIG. 15A is a schematic view of a universal testing machine (UTM) according to certain embodiments of the disclosure.

In certain embodiments, an anchor cage assembly 1400 as shown in FIG. 14A is disclosed that can be employed to conduct the pull-out testing using a Universal Testing Machine (UTM) 1500 as shown in FIG. 15A, eradicating the need of separate pull-out testing devices. Further, in other embodiments, 8 mm, 10 mm and 12 mm diameter concrete anchors may be used, keeping constant the embedment length and concrete strength.

The pull-out load strength versus rebound value relationship for each diameter anchor is disclosed with correlation of more than 90%. In certain embodiments, a correlation among the pull-out load carrying capacity, P of pre-construction installed concrete anchors and the rebound value, R of the Schmidt hammer is disclosed. Various factors affecting the correlation relationship are alignment of the anchors, diameter of the anchors, embedment length of the anchors, and concrete strength. In some embodiments, three diameters of concrete anchors may be used, namely 8 mm, 10 mm, and 12 mm to determine the co-relation between pull-out load carrying capacity, P and rebound value, R.

In certain embodiment, for example, fifty-four concrete cylindrical specimens of 150×300 mm, may be prepared using ordinary Portland® cement (Type-I) having the chemical composition by percentage weight as follows: CaO=64.3, $SiO_2$=22, $Al_2O_3$=5.64, $Fe_2O_3$=3.8, $K_2O$=0.36, MgO=2.11, $Na_2O$=0.19, equivalent alkalis ($Na_2O$+ $0.658K_2O$)=0.42, loss on ignition=0.7, $C_3S$=55, $C_2S$=19, $C_3A$=10 and $C_4AF$=7. The water content is 160 kg/m$^3$, cement 288 kg/m$^3$, air entrained 4.1%, sand and gravel 828 kg/m$^3$ and 1043 kg/m$^3$ respectively and the water-cement ratio is 0.40. The slump is 100±25 mm and 7 day compressive strength is 28.5 MPa. Dune sand may be used as fine aggregate having bulk specific gravity and absorption of 2.62 and 0.62%, respectively. Crushed limestone may be used as coarse aggregate having bulk specific gravity and absorption of 2.60 and 1.08%, respectively. Further, coarse aggregate grading requirement may be fulfilled as per ASTM C33 by selecting sieve size number 56 and aggregate size of 19 and 9.5 mm proportioned to 85 and 15% by mass, respectively. Further, 8 mm, 10 mm and 12 mm steel bolts may be used having a length of 152.4 mm. One-third of the total length of each anchor bolt 305 in this example may be embedded in a concrete cylinder 315 and held in place using metal guide wires 310 (steel), as shown in FIG. 3.

Figure 3:
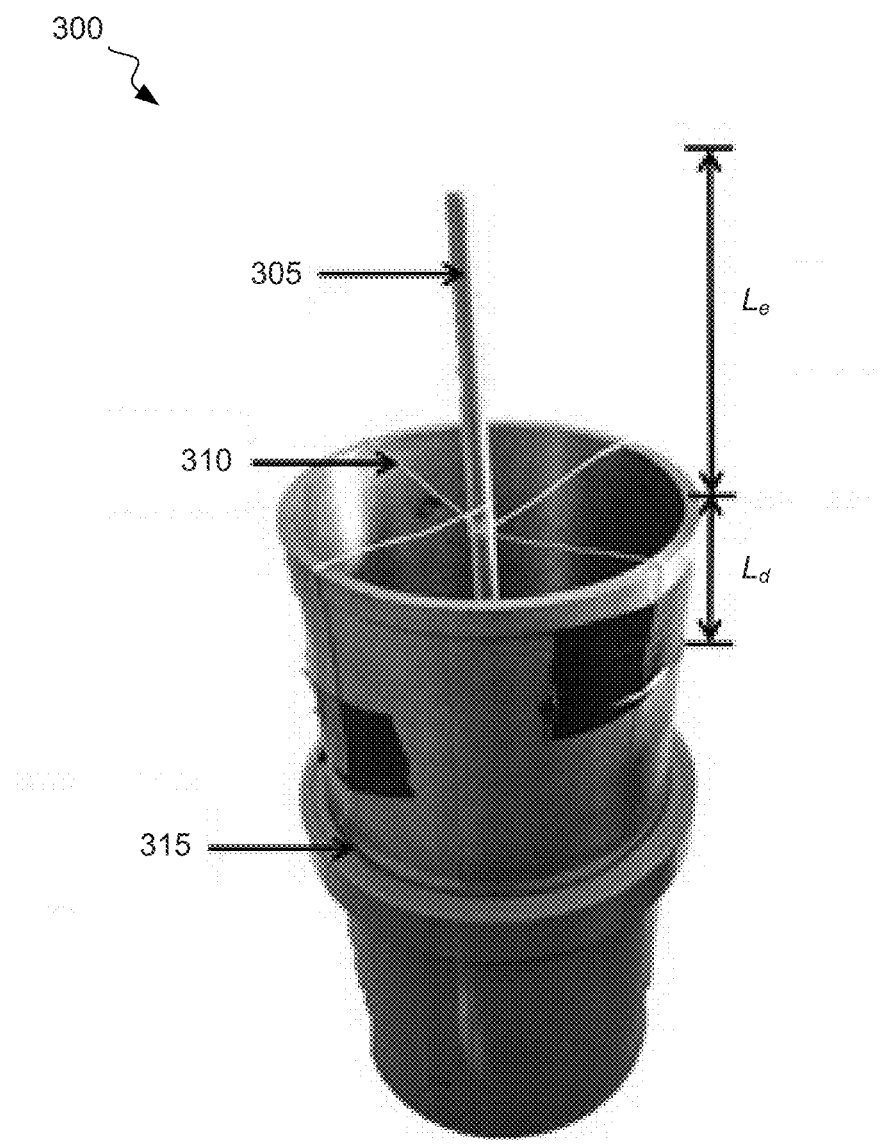
FIG. 3 is an illustrative view of an anchor bolt embedment assembly according to certain embodiments of the disclosure.

FIG. 3 is an illustrative view of an anchor bolt embedment assembly 300 according to certain embodiments of the disclosure. In FIG. 3, assembly 300 may include an anchor bolt 305, guide wires 310, and a concrete cylinder mold 315.

In certain embodiments, bolt 305 may be embedded within concrete cylinder mold 315 by a length, $L_d$ while having an exposed length, $L_e$. Guide wires 310 may include at least three steel wires to align bolt 305 during embedment into concrete cylinder set in mold 315 while the concrete is wet and setting.

The details of experimentation including specimen preparation, casting, curing procedure and testing of compressive and pull-out strength are described in commonly owned, Saleem, S., Walid, A., Nabil, A and Hassan, H.: "Non-Destructive Testing Method to Evaluate the Load Carrying Capacity of Concrete Anchors", ASCE Journal of Construction Engineering and Management, 2015, herein incorporated by reference. Each anchor bolt 305 may be centered in the cylindrical mold 315 during fresh state of concrete and after the a curing period of about 28 days, five rebound readings may be recorded on top of bolt 305 at its distal end representing a set with an average value used for data analysis. Instead of relying on the manufacturer mentioned impact energy value, the actual amount of impact load imparted was verified by using an N Type Schmidt Hammer. The reasoning behind this was to take into account the inherent variation of the rebound hammer and the variations resulting from wear and tear after owing to consistent use as recommended by the manufacturer that recommends the user to verify the readings after about 2000 strokes.

Figure 4:
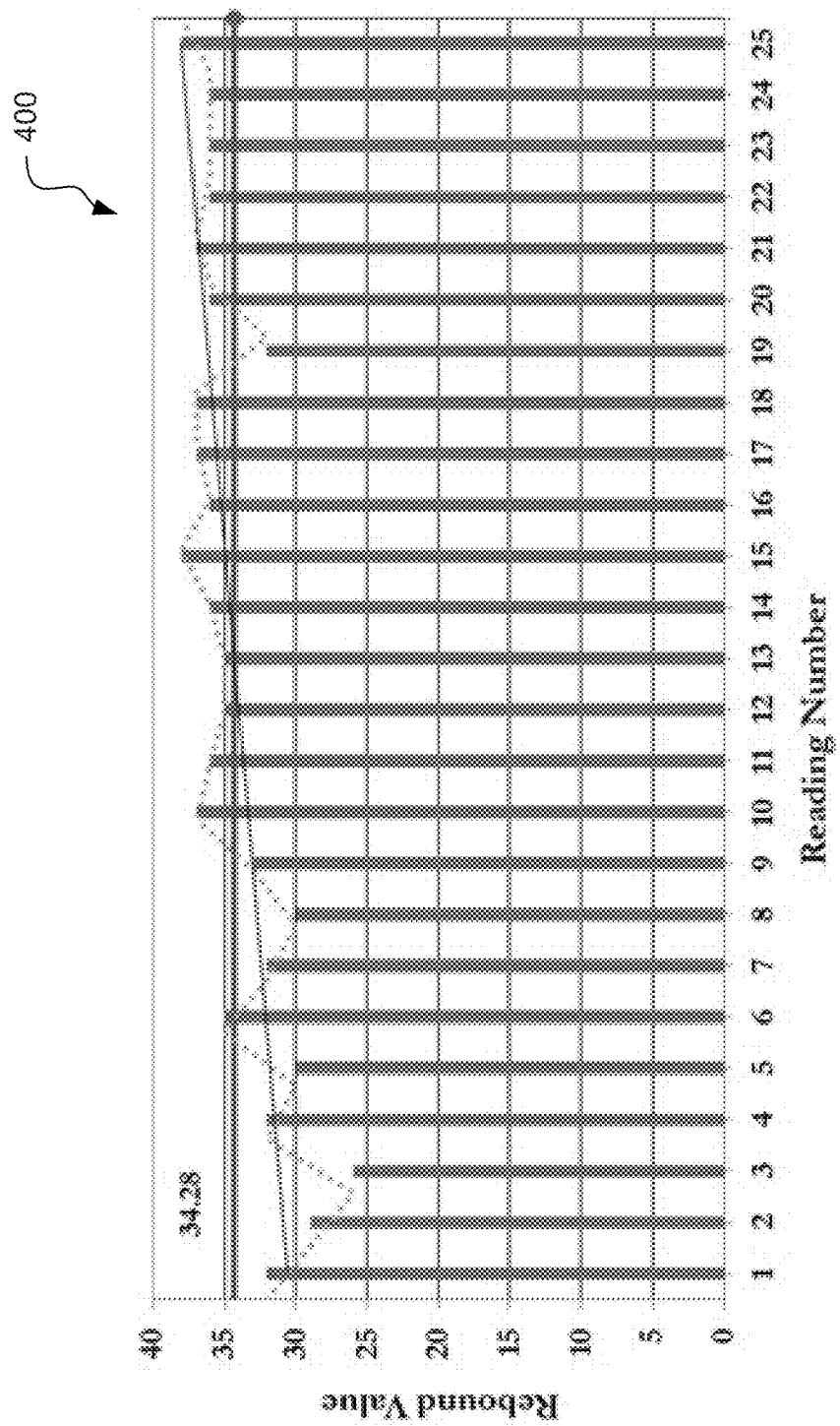
FIG. 4 is a bar graph illustrating a variation in rebound value readings according to certain embodiments of the disclosure.

FIG. 4 is a bar graph 400 illustrating a variation in rebound value readings according to certain embodiments of the disclosure. In FIG. 4, twenty-five readings were considered as a single set to calculate the average value, about 34.28, in this regard FIG. 4 represents the variation in the rebound number of the Schmidt hammer.

Figure 5:
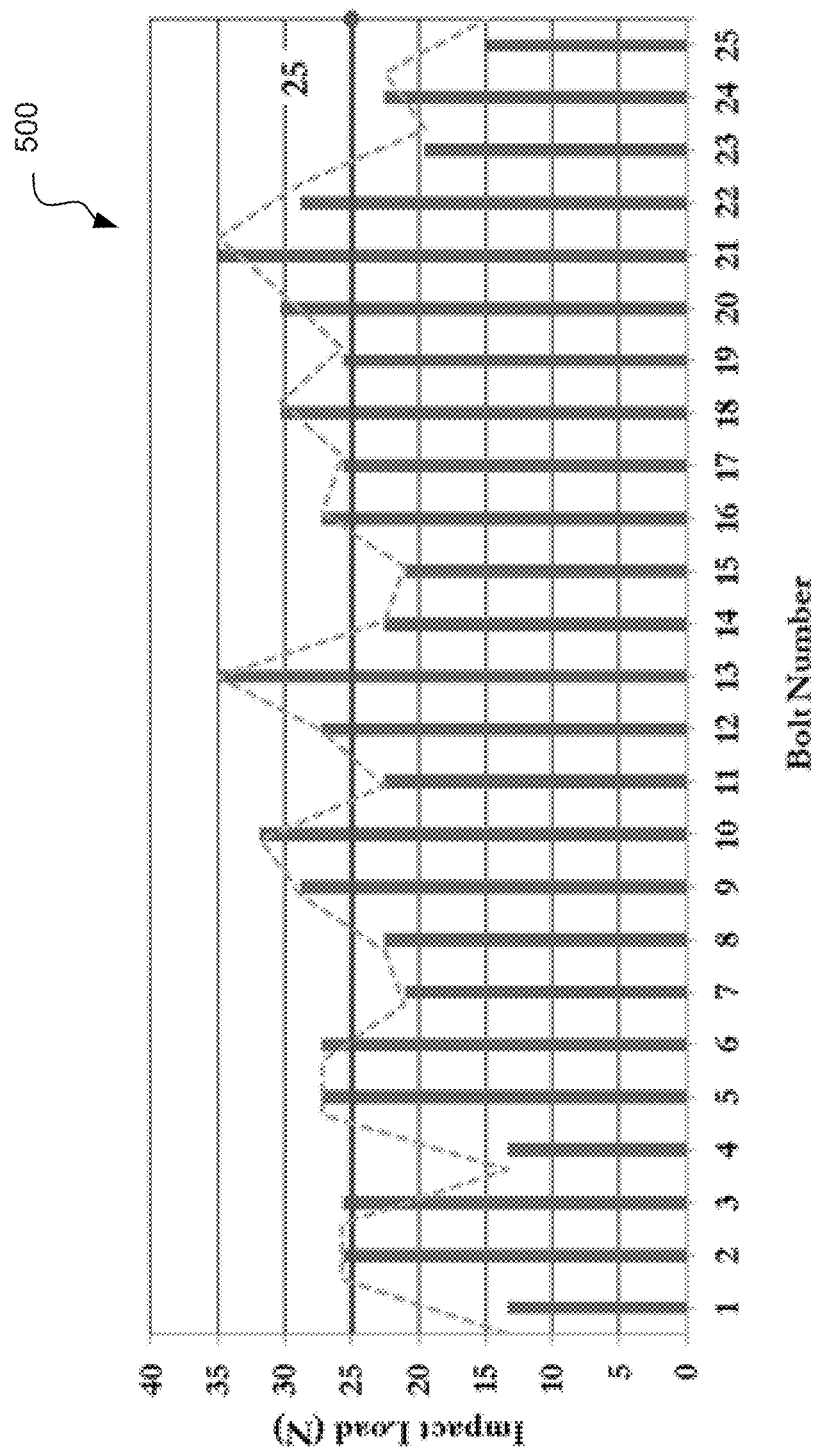
FIG. 5 is a bar graph illustrating a variation in impact energy recording by a load cell according to certain embodiments of the disclosure.

FIG. 5 is a bar graph 500 illustrating a variation in impact energy recording by the load cell 200 according to certain embodiments of the disclosure. In FIG. 5, the variation in impact load imparted by the Schmidt hammer 210 is recorded by the load cell 200 of FIG. 2. The average impact energy recorded was 0.191 kg-m which is about 16% lower than the manufacturer specified impact energy i.e., 0.227 kg-m. For all further calculations the measure of impact energy was utilized. It can be seen that as predicted there exist a variation in the Schmidt Hammer readings. In order to overcome the variation the average value for all the further calculations may be used.

Figure 6:
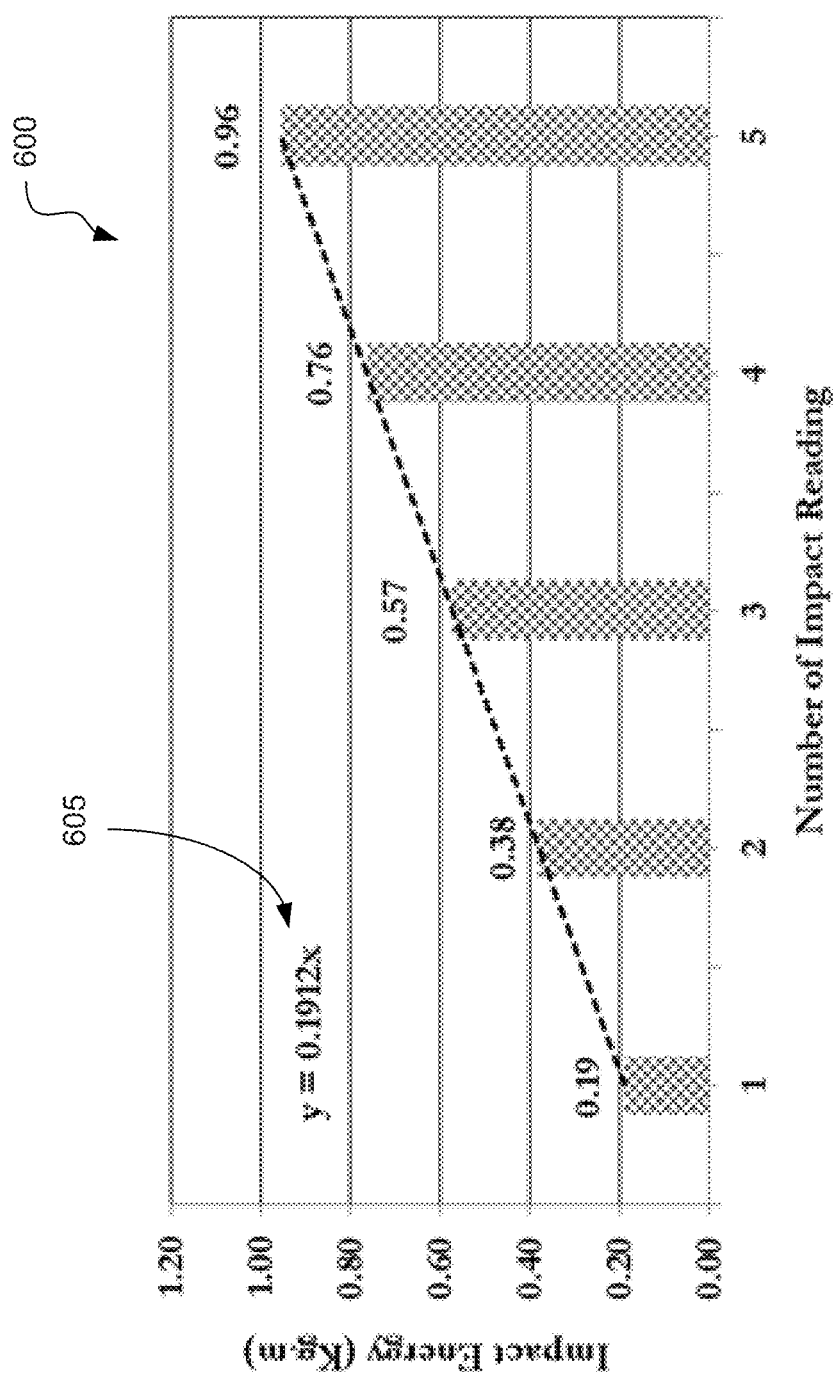
FIG. 6 is a bar graph illustrating a cumulative impact energy imparted on an anchor bolt according to certain embodiments of the disclosure.

FIG. 6 is a bar graph 600 illustrating a cumulative impact energy imparted on an anchor bolt 305 according to certain embodiments of the disclosure. In FIG. 6, each bolt 305 was subjected to five impact loadings by the rebound hammer (210) hence the cumulative amount of impact energy should be taken into consideration when analyzing the bond performance of these anchor bolts (305). Graph 600 shows a projected linear relationship 605 among the five impact loadings.

Figure 7:
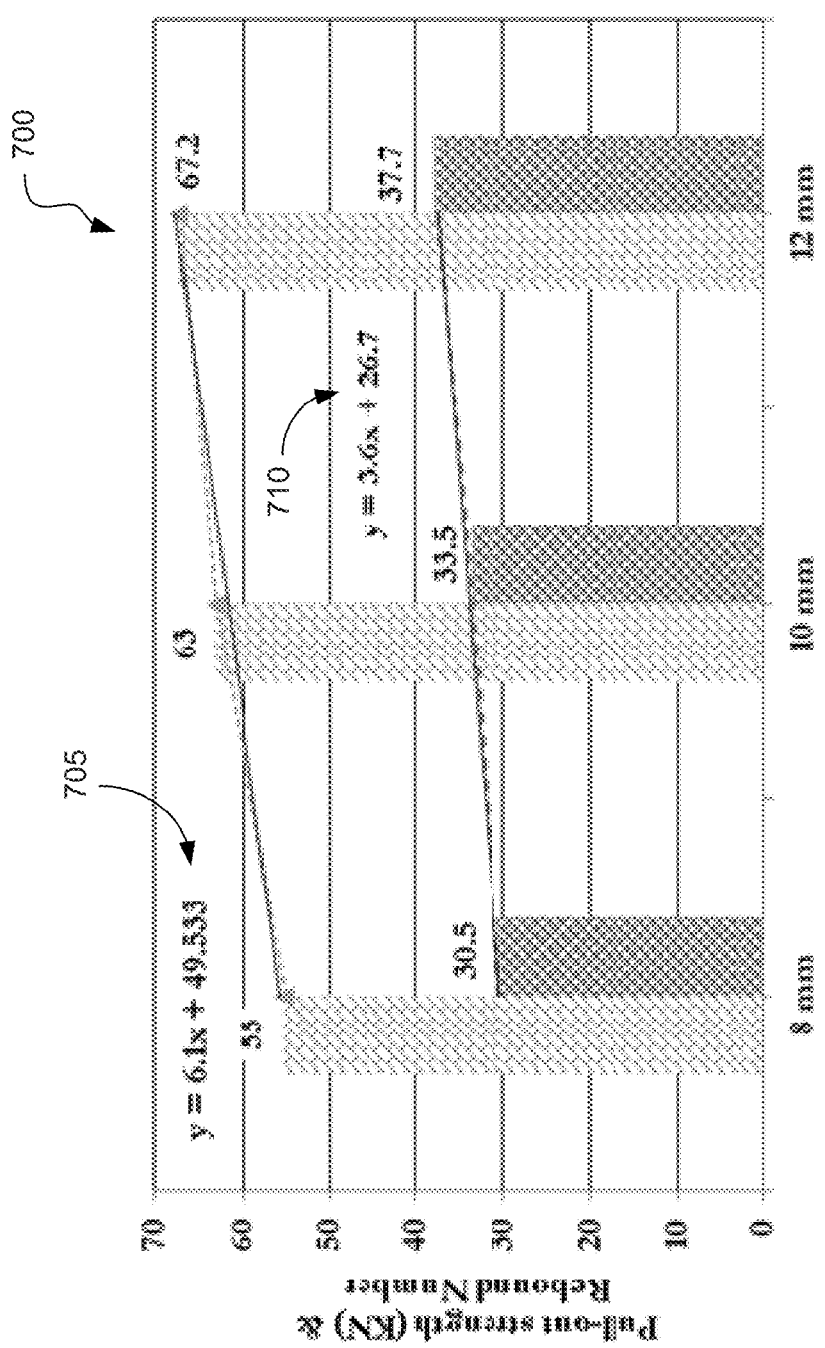
FIG. 7 is a bar graph illustrating a relationship between rebound value and pull-out strength to anchor bolt diameter according to certain embodiments of the disclosure.

FIG. 7 is a bar graph 700 illustrating a relationship between rebound value and pull-out strength to anchor bolt diameter according to certain embodiments of the disclosure. FIG. 7 depicts the average test results of 15 anchored specimens for pull-out strength and rebound number correlated with respect to bolt diameter (8 mm, 10 mm, and 12 mm). It can be seen from FIG. 7 that as the bolt diameter increases the rebound number, R and the load carrying capacity increases in a linear fashion at 705 and 710, respectively. The rebound number increases by 12.7% and 6.3% for 8 mm to 10 mm and from 10 mm to 12 mm increase in diameter of the bolt while the pull-out strength increases by 9% and 11.2%, respectively. This increase in pull-out strength can be attributed to increase in circumferential area for increased bond strength. However, it is to be highlighted that as the diameter of the anchor bolt increases the capability to transfer the impact energy to surrounding concrete increases, it is to be noted that the impact loading is applied on top of the bolt and not directly on the concrete surface. It is evident that for smaller bolts the impact energy causes micro-fracture at the interface of the bolt and surrounding matrix. This phenomenon also highlights the limitation that the Schmidt hammer 210 can be used to measure the bond strength for small to medium sized anchor bolt as for larger diameter bolts the hammer 210 would be unable to induce large enough impact loading that could give an indication about the bond strength of the bolt. Hence for larger bolts and steel anchor rods used in tunneling industry a larger impact loading device is necessary.

Thus, by using the rebound number it is possible to predict defects under the surface such as porosity owing to poor quality of concrete, micro-cracking at the interface of bolt and concrete matrix, bolt misalignment and water ingress, as all these defects lead to lower rebound numbers. Since the Schmidt hammer 210 imparts approximately 0.96 kg-m of energy on each bolt 305, where upon a bolt with proper alignment, embedded in good quality concrete is successfully able to transfer this energy to the surrounding concrete. This leads to large rebound number, R. However for a bolt embedded in porous concrete or having any hidden defects or with misalignment, the impact energy is not successfully transferred to the surrounding concrete leading to a reduction in rebound number, R. In this regards an analytical model capable of taking into consideration the bolt alignment, concrete quality, micro-fracturing of the interface and bond performance of the bolt, detailing the pull-out process is presented in the proceeding section.

Figure 8:
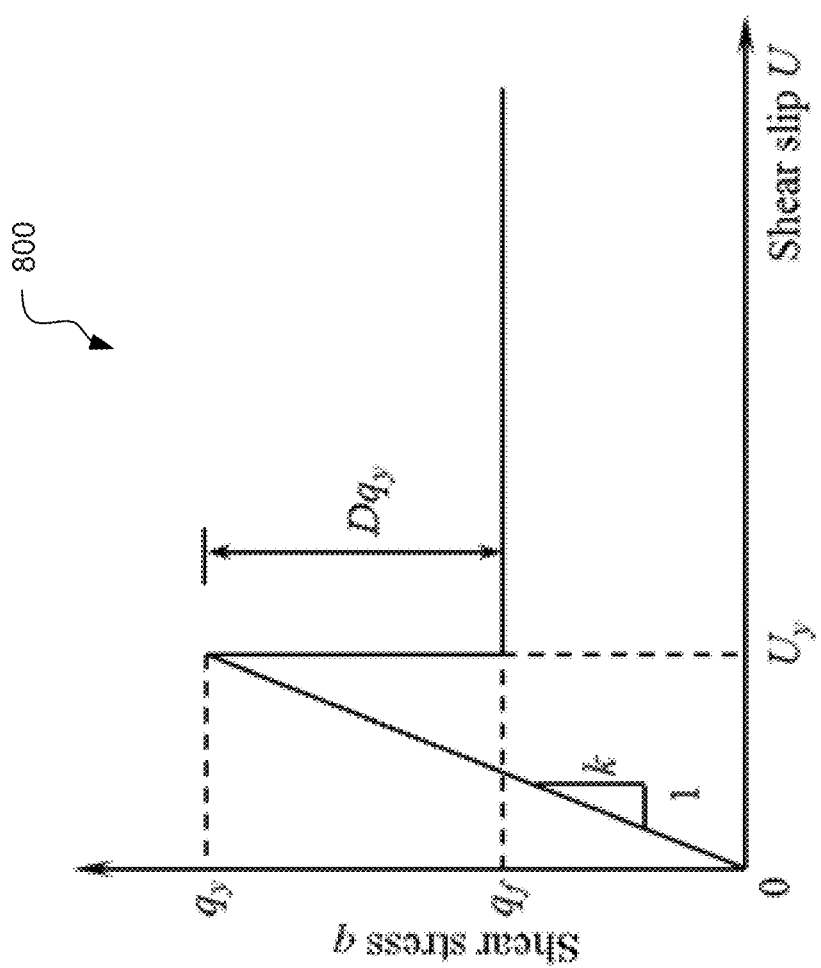
FIG. 8 is a graphical plot of shear slip verses shear stress showing a constitutive relationship of an anchor bolt and a surrounding matrix according to certain embodiments of the disclosure.

FIG. 8 is a graphical plot 800 of shear slip verses shear stress showing a constitutive relationship of an anchor bolt 305 and a surrounding matrix according to certain embodiments of the disclosure. In FIG. 8, an interfacial bond exists between the bolt and surrounding concrete. The bond can be categorized in two zones, the first being the initial perfect zone without any defects and micro-cracking and second being the de-bonded zone as a result of impact energy. It is highlighted that upon impact loading the micro-cracking would be initiated and the bond strength in the de-bonded zone would be reduced. This constitutive relationship is as depicted in FIG. 8 and equations (1) to (21) discussed below.

Figure 9:
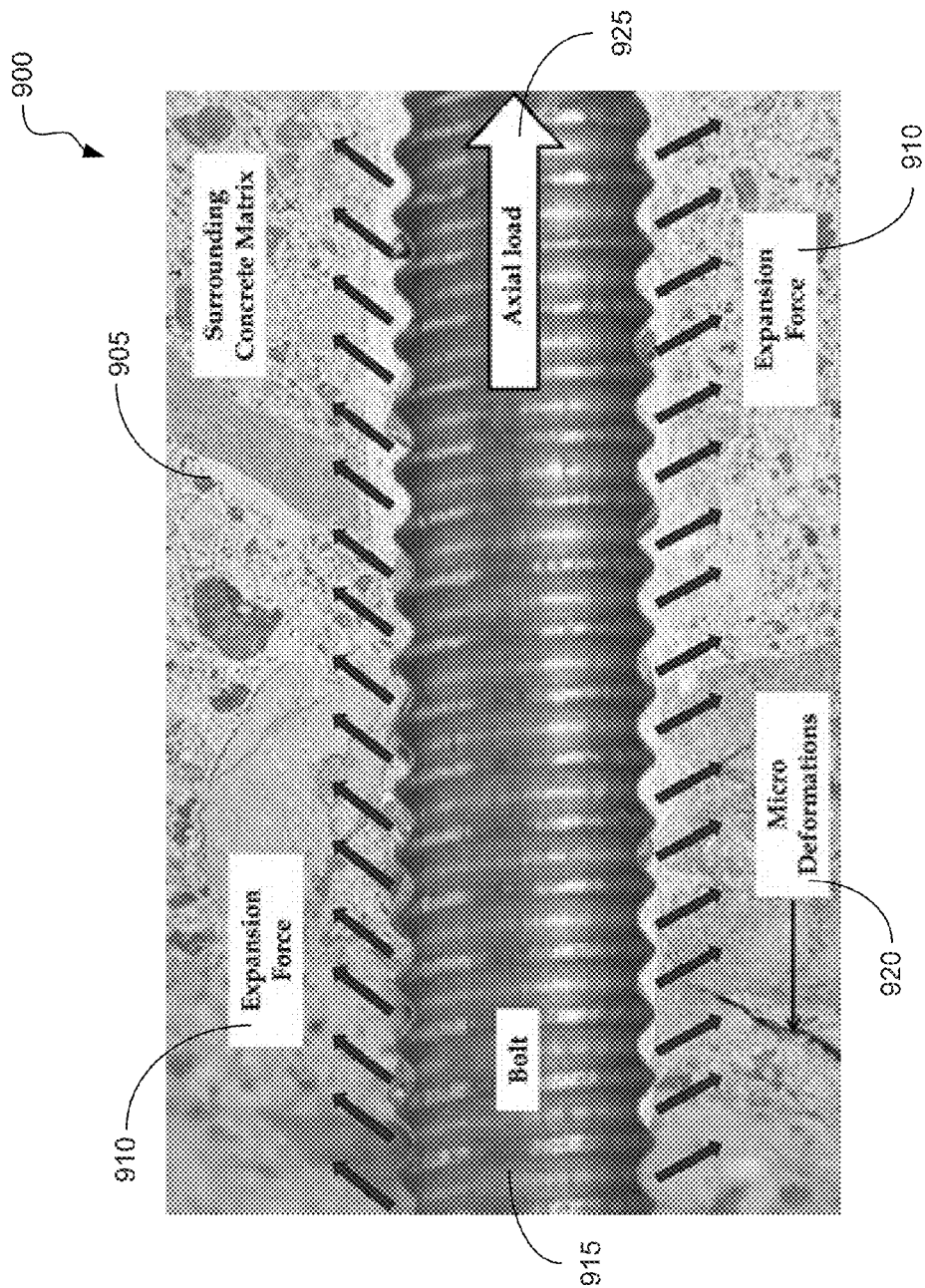
FIG. 9 is an illustrative view of an anchor bolt pull-out mechanism according to certain embodiments of the disclosure.

FIG. 9 is an illustrative view of an anchor bolt 915 pull-out mechanism 900 according to certain embodiments of the disclosure. In FIG. 9, a de-bonded zone is depicted with a frictional interlocking between the threads of bolt 915 and the surrounding concrete 905 exists at an expansion force 910 where as in the bonded zone a perfect bond between the bolt 915 and surrounding concrete 905 is visualized while under an axial load 925. Further, axial load 925 may result in micro deformations 920 in the concrete 905.

Figure 10:
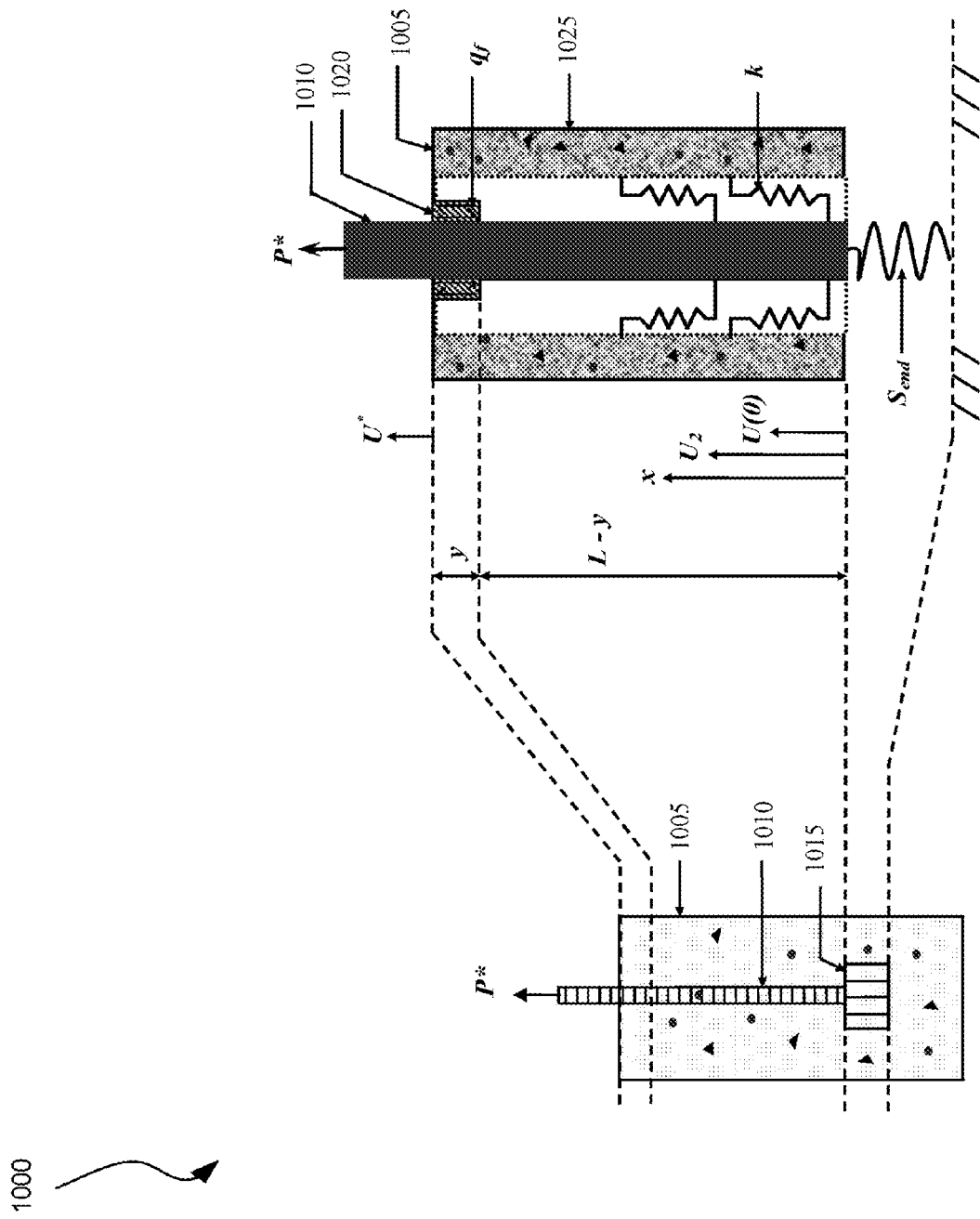
FIG. 10 is an illustrative view of an anchor bolt pull-out model with interfacial cracking according to certain embodiments of the disclosure.

FIG. 10 is schematic view of an anchor bolt pull-out model 1000 with interfacial cracking according to certain embodiments of the disclosure. In FIG. 10, a bolt 1010 of length L and an anchor head 1015 is embedded in a concrete cylinder 1005 having a rigid matrix 1025. The concrete cylinder 1005 is assumed to be rigid except a thin interfacial layer idealized as an interface with shear stiffness, k. Various types of bolt geometry may be used, such as hooked, inverted, and straight. The bolt end may be modeled as a spring with a constant, $S_{end}$. Bolt 1010 is assumed to have a constant cross-sectional area, $A_b$, and an elastic modulus $E_b$. It is assumed that de-lamination owing to micro-deformations at the interface of concrete cylinder 1005 and bolt 1010 has occurred as a result of the impact loading induced by the Schmidt hammer 210 over a length, y, starting at x=L. Furthermore, a constant shear force is acting on a de-laminated zone. The constitutive relationship is expressed by equations (1) and (2).

$$q = kU(x) \quad 0 < x < (L-y) \tag{1}$$

$$q = q_f (L-y) < x < L \tag{2}$$

where q is the shear force per unit length acting on the bolt, $q_f$ is the frictional shear force per unit length, and U(x) is the bolt pull-out displacement. The constitutive relationship, as shown in FIG. 8, can be explained as a linear branch up to the shear strength followed by progress in de-laminated zone at the interface and a sudden drop $Dq_y$ in the shear stress followed by constant shear stress acting along the de-laminated interface. Also, $q_y$ is the maximum shear force per unit length and D is the reduction factor to take into account the reduced bond condition after de-laminating representing stress release owing to progress in cracking.

$$P' - q = 0 \tag{3}$$

where the prime represents the differentiation with respect to x. Then the following equation is obtained;

$$P = E_b A_b U' \tag{4}$$

where $E_b A_b$ is the anchor bolt stiffness of the anchor bolt.

$$U'' - \varpi^2 U = 0 \quad 0 < x < (L-y) \tag{5}$$

$$U'' - \frac{q_f}{E_b A_b} = 0 \quad (L-y) < x < L \tag{6}$$

where $\varpi$ is defined as $$\varpi = \sqrt{\frac{k}{E_b A_b}} \tag{7}$$

When P* as the pull-out force at x=L, the boundary conditions and the continuity conditions at x=L−y are prescribed as $$S_{end} U(0) = P(0) \tag{8}$$

$$E_b A_b U'(L) = P^* \tag{9}$$

$$U_i(L-y)^- = U_i(L-y)^+ \tag{10}$$

$$U'(L-y)^- = U'(L-y)^+ \tag{11}$$

Solution of the above equations results in bolt pull-out displacement;

$$U(x) = \frac{P^* - q_f y}{E_b A_b \varpi} \left\{ \frac{\cosh \varpi x}{\Gamma_1} + \frac{\sinh \varpi x}{\Gamma_2} \right\} \quad 0 < x < (L-y) \tag{12}$$

$$U(x) = \frac{q_f x^2}{2E_b A_b} + \frac{P^* - q_f L}{E_b A_b} x - \quad (13)$$
$$\frac{q_f (L-y)^2}{2E_b A_b} + \frac{P^* - q_f y}{E_b A_b \varpi} \Gamma_3 - \frac{P^* - q_f L}{E_b A_b}(L-y)$$
$$(L-y) < x < L$$

$$\Gamma_1 = \frac{S_{end}}{E_b A_b \varpi} \cosh\varpi(L-y) + \sinh\varpi(L-y) \quad (14)$$

$$\Gamma_2 = \cosh\varpi(L-y) + \frac{E_b A_b \varpi}{S_{end}} \sinh\varpi(L-y) \quad (15)$$

$$\Gamma_3 = \frac{\cosh\varpi(L-y)}{\Gamma_1} + \frac{\sinh\varpi(L-y)}{\Gamma_2} \quad (16)$$

$$U^* = \frac{P^* - q_f y}{E_b A_b \varpi} \Gamma_3 + \frac{P^* - \frac{1}{2} q_f y}{E_b A_b} \quad (17)$$

The de-lamination criterion is expressed in terms of shear force per unit length q, and it is assumed that de-lamination starts when q reaches a critical value $q_y$.

$$q_f = D q_y \quad (18)$$

where, after de-bonding occurs, D is assumed to be constant $D_o$ up to the peak for matrix:

$$D = D_o \quad 0 \leq D_o \leq 1 \quad (19)$$

The coefficient D as depicted in FIG. 8 represents the shear transfer capability which depends on interlocking between the bolt treads and the surrounding concrete matrix. The condition for de-bonding, $q=q_y$, at $x=L-y$ is written as $$P^* = q_f y + \frac{q_y}{\varpi} \left\{ \frac{\Gamma_1 \Gamma_2}{\Gamma_4} \right\} \quad (20)$$

$$\Gamma_4 = \Gamma_1 \sinh\varpi(L-y) + \Gamma_2 \cosh\varpi(L-y) \quad (21)$$

The load at which de-lamination starts is obtained by substituting y=0 in the above equation. The presented model equations (17) and (20) can be used to predict the final pull-out load-deformational response of anchor bolt 1010. The process is initiated with the small micro-fracture cracks combining under the action of applied load to form de-bonding at the interface of bolt 1010 and rigid matrix 1025. Upon further increase in loading the de-bonding zone 1020 starts to propagate downward towards the bottom part of the bolt 1010. The ultimate pull-out load carrying capacity depends on the path travelled by the de-bonding zone 1020, that is, the embedment length and diameter of the bolt 1010. Upon complete de-bonding, sudden failure occurs and the sustainable load drops. After sudden failure, a successive pull-out process continues until the anchor is completely pulled out of concrete. Frictional force generated by the interlocking between the groves of the anchor bolt and the matrix exists in the de-bonded zone 1020 after completion of de-bonding. The elongation of the anchor bolt 1010 may be negligible because the elongation is too small compared to the original anchor length and total displacement.

Figure 11A:
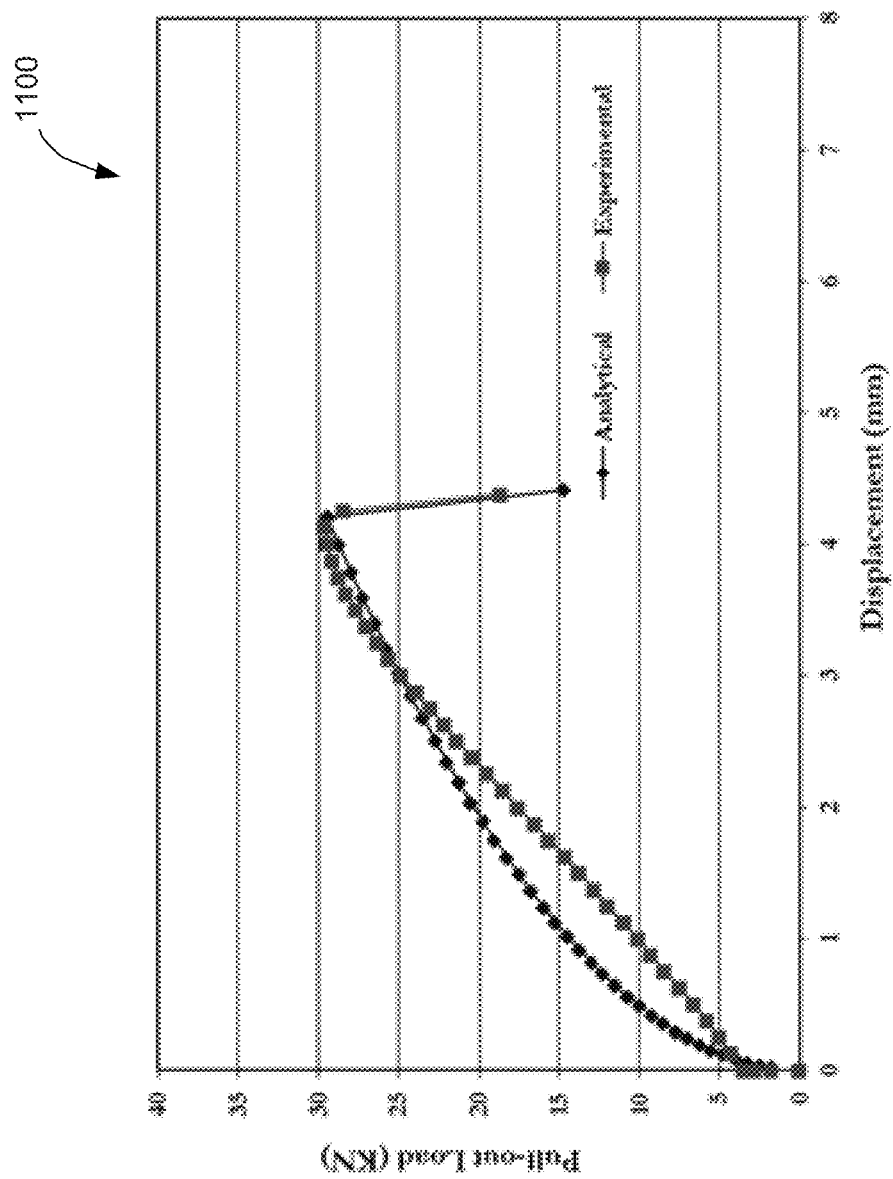
FIG. 11A is graphical plot of displacement verses pull-out load comparing experimental and analytical load-displacement response for an 8 millimeter (mm) diameter anchor bolt according to certain embodiments of the disclosure.
Figure 11B:
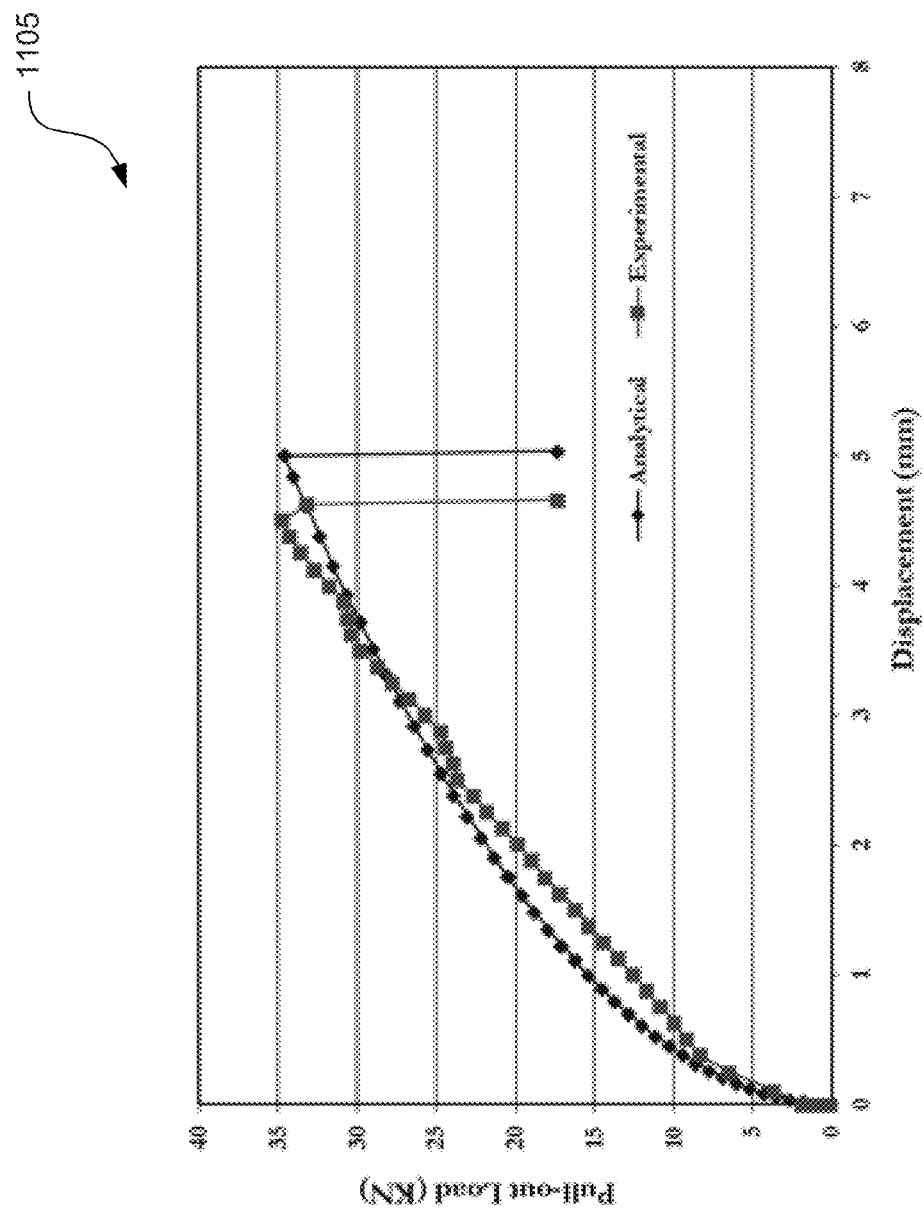
FIG. 11B is graphical plot of displacement verses pull-out load comparing experimental and analytical load-displacement response for a 10 mm diameter anchor bolt according to certain embodiments of the disclosure.
Figure 11C:
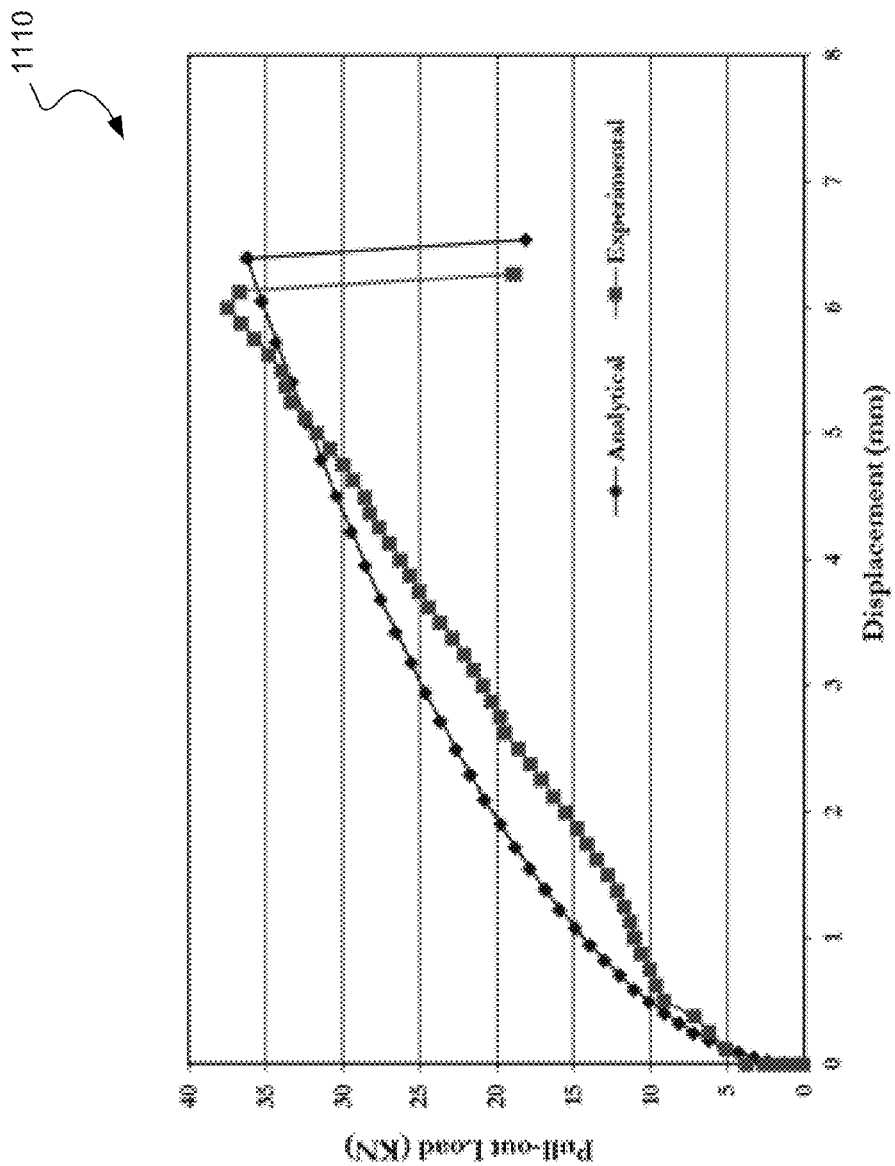
FIG. 11C is graphical plot of displacement verses pull-out load comparing experimental and analytical load-displacement response for a 12 mm diameter anchor bolt according to certain embodiments of the disclosure.

FIG. 11A is graphical plot 1100 of displacement verses pull-out load comparing experimental and analytical load-displacement response for an 8 millimeter (mm) diameter anchor bolt according to certain embodiments of the disclosure. FIG. 11B is graphical plot 1105 of displacement verses pull-out load comparing experimental and analytical load-displacement response for a 10 mm diameter anchor bolt according to certain embodiments of the disclosure. FIG. 11C is graphical plot 1110 of displacement verses pull-out load comparing experimental and analytical load-displacement response for a 12 mm diameter anchor bolt according to certain embodiments of the disclosure.

FIGS. 11A, 11B, and 11C illustrate the comparison of analytical and experimental pull-out load—deformation response for 8 mm, 10 mm, and 12 mm diameter anchor bolts. The horizontal axis represents the pull-out displacement while the vertical axis presents the pull-out load. The ratio r/L may be 0.08, 0.1, and 0.12 respectively where r represents the radius of the anchor bolt and L represents the embedment length which was 50 mm for all three cases. The elastic modulus of bolt, $E_b$, was taken as $2.0 \times 10^5$ N/mm$^2$. In some embodiments, an estimate of the initial value of maximum shear force per unit length $q_y$, was approximated by the maximum measured pull-out force from experimental data per unit length of the anchor bolt 1010. The material constants control the maximum pull-out force at the anchor end as represented by $S_{end}$. The shear stiffness of the interfacial zone where micro-cracking is initiated owing to impact loading is taken as $k=0.2 \times 10^5$ N/mm$^2$. The value of anchor bolt end shape depends on the shape of the anchor bolt 1010 and may be approximated independently by considering geometry of the anchor bolt 1010. In case of straight anchor bolts this value can be reduced to negligible, however for anchor bolts with hooks or a bend at the end this value should be experimentally calculated. In certain embodiments, the results for the value of $S_{end}$ is taken from experimental results for fiber end conditions.

It can be seen in FIGS. 11A, 11B, and 11C that initially upon increase in loading the pull-out displacement is negligible, however after gradual increase in the pull-out loading the displacement start to increase till the failure load is reached and for the anchor bolt 1010 complete de-bonding occurs, leading to a sudden drop in load value. The sequence is followed by the gradual pull-out of the anchor bolt 1010 however the load carrying capacity is completely exhausted. The above-mentioned description of the pull-out displacement response can be explained by the phenomenon that initially the anchor bolt 1010 is without any defect, however upon the introduction of impact loading micro-cracking can occur alongside the embedded anchor. Upon gradual increase in loading these micro-cracks bridge together and de-bonding progresses along the interfacial zone as this presents the weakest zone as per energy criterion for crack propagation. However, once the de-laminating crack reaches the bottom of bolt 1010, sudden reduction occurs in the deformational response caused by the loss of rib force.

From the FIGS. 11A, 11B, and 11C it is evident that the present disclosure is capable of predicting or estimating the pull-out response of bolts. Furthermore, it can be concluded that the present disclosure is able to accurately predict or estimate the maximum load carrying capacity and can take into consideration the micro-cracking, bolt diameter, embedment length, bolt alignment, and defects in concrete. The peak variation in the pull-out displacements is about 4%.

Thus, the impact loading is such that imparted by the Schmidt rebound hammer. An analytical model capable of taking into consideration bolt diameter, end shape effect, embedment length, alignment, micro-defects and interfacial bond is also presented. The following conclusions can be drawn from the presented result and discussion. It is possible to identify defects in installed bolt with the help of Schmidt hammer rebound number. Evidence has shown that bolts with misalignment, micro-cracking and poor quality of surrounding concrete depict lower rebound value as they are unable to transfer impact loading to the surrounding concrete. On the other hand, bolts with good quality of surrounding concrete and proper installation depict higher rebound numbers owing to the ability to transfer impact loading to the surrounding concrete.

As the bolt diameter increases the pull-out load carrying capacity also increases owing to larger bond strength.

The present disclosure is successfully able to take into consideration bolt diameter, end shape, embedment length, alignment, micro-defects and is able to predict or estimate the maximum experimental pull-out load carrying capacity of bolts.

Figure 12A:
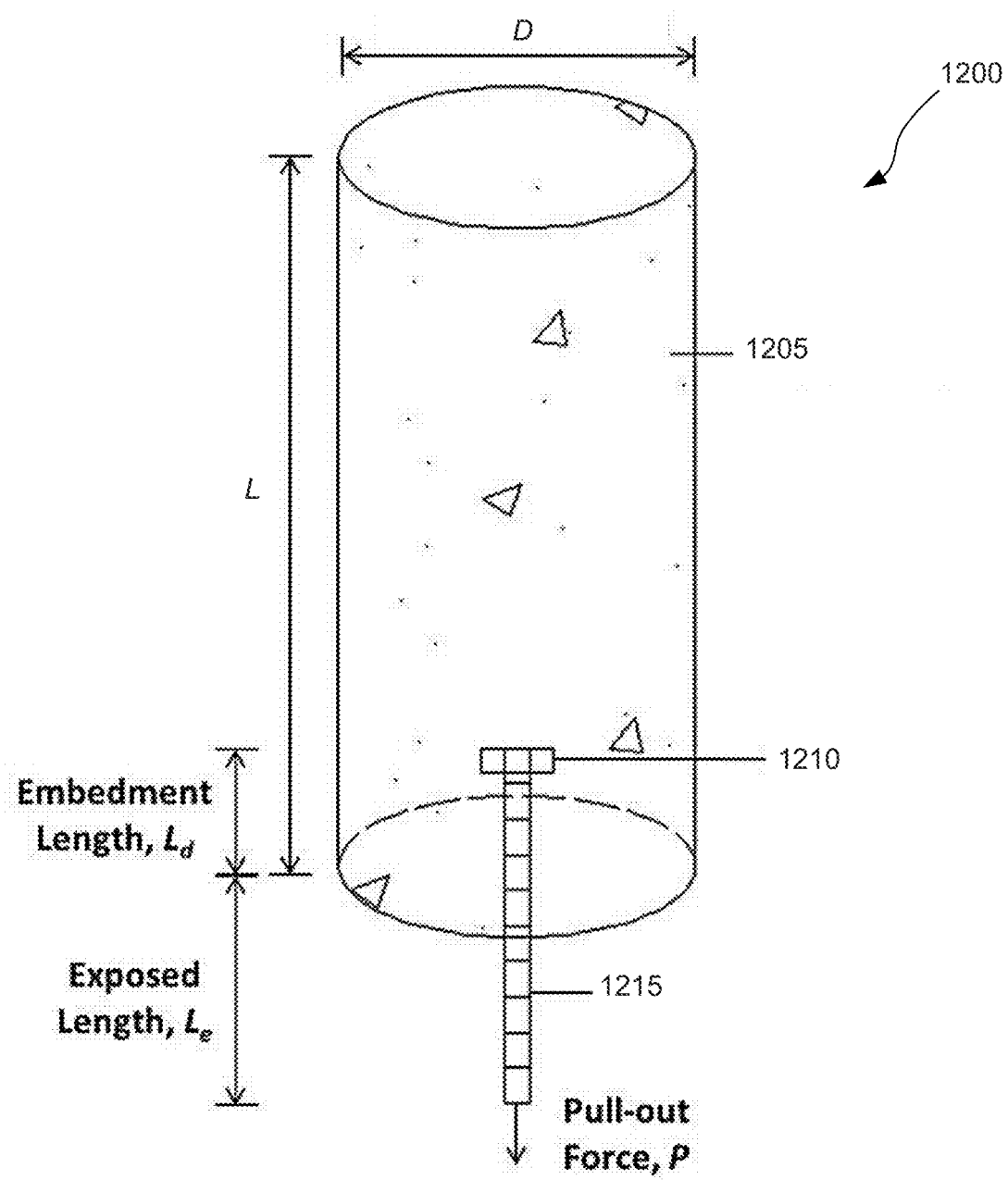
FIG. 12A is a schematic diagram illustrating an anchor bolt installation in a concrete cylinder sample according to certain embodiments of the disclosure.

In some embodiments, fifty concrete cylindrical specimens sized 150×300 mm may be prepared using ordinary Portland cement (Type-I) with water content 160 kg/m$^3$, cement 288 kg/m$^3$, air entrained 4.1%, sand and gravel 828 kg/m$^3$ and 1043 kg/m$^3$ respectively and the water-cement ratio (w/c) may be 0.40. The slump was 100+25 mm and 7 day compressive strength was 28.5 MPa. The maximum size of the coarse aggregate may be, for example, 20 mm, while dune sand was used as fine aggregate. Curing of the concrete cylinders with embedded anchor bolts as shown in FIG. 12A may be conducted in curing tank at room temperature for 28 days. After completion of curing rebound hammer readings may be recorded on top of the anchor bolt 1215 as shown in FIG. 12A. For example, five reading may be recorded as each set with average value used for data analysis as shown in Table 1, 2 and 3. During the rebound reading recording procedure the Schmidt hammer 210 was kept vertical by visual inspection and the hammer tip was kept perpendicular to the anchor bolt 1215. It was observed during recording the rebound reading that anchor bolts with slight misalignment resulted in lower readings furthermore the anchor bolt with misalignment greater than 15° was not suitable for rebound testing. The tip of the rebound hammer slipped during impact for anchor bolt with large misalignment.

FIG. 12A is a schematic diagram illustrating an anchor bolt installation 1200 in a concrete cylinder sample 1205 according to certain embodiments of the disclosure. In FIG. 12A, concrete cylinder sample 1205 may have a diameter, D and a length, L. Concrete cylinder sample 1205 may include an embedded anchor bolt 1215 with an anchor bolt head 1210. Anchor bolt 1215 includes an embedment length, $L_d$ and an exposed length, $L_e$.

Figure 12B:
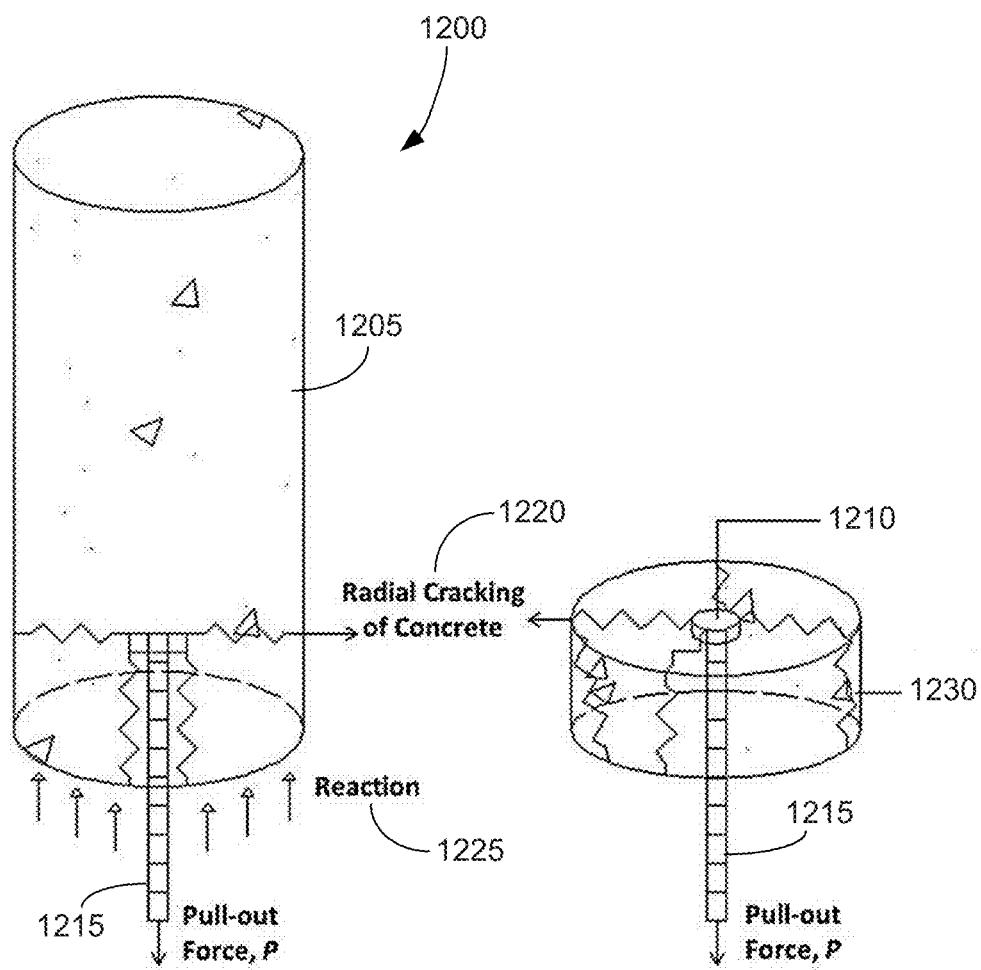
FIG. 12B is a schematic diagram illustrating an internal force distribution and failure pattern according to certain embodiments of the disclosure.

FIG. 12B is a schematic diagram illustrating an internal force distribution and failure pattern according to certain embodiments of the disclosure. FIG. 12B depicts the internal stress distribution, radial cracking pattern 1220, and circumferential cracking 1230 of the test sample 1205. Traditional anchor pull-out tests result in cone type failure of concrete, however owing to the reaction provided by the base plate 1420 of the anchor cage 1400 vertical crushing of the concrete may be expected (see FIG. 14A). Furthermore, on the top of anchor bolt head 1210 radial stress distribution may result in circumferential cracking 1230.

The concrete on top of the anchor bolt head 1210 acted as a dead load. In certain embodiments, it was observed that the rebound value, R of the anchor bolt 1215 is deeply affected by the embedment length $L_d$, anchor bolt diameter, concrete strength, and the interfacial bond between the anchor bolt 1215 and the surrounding concrete.

In some embodiments, the interfacial bond between the anchor bolt and the surrounding concrete can be categorized in two types. The frictional bond, which exist between the anchor bolt and concrete and the mechanical interlocking bond between the anchor bolt threads and surrounding materials. It is seen that prior to cracking mechanical bond is responsible as the material interlocks and transmits load to the surrounding concrete, however upon the commencement of micro-cracking the mechanical interlocking bond begins to lose its strength and the frictional bond springs into action. This explanation can be used to explain the cracking pattern as shown in FIG. 12B. It is seen that as the anchor bolt begins to slip, vertical cracks indicating the loss of mechanical bond appear. These vertical cracks appear owing to expansion of surrounding concrete and frictional cracking of concrete. The vertical cracks are immediately followed by the radial cracking at the top of the anchor bolt head. This delay in appearance of radial cracking can be explained by the fact that since the cracking propagates from bottom of anchor bolt to top and owing to slight elongation of the bolt the radial cracks appear after the vertical cracking. Furthermore it has been seen that after the vertical cracking the crushing of concrete occurs at the final stage of pull-out when the frictional bond is dominant.

Figure 12C:
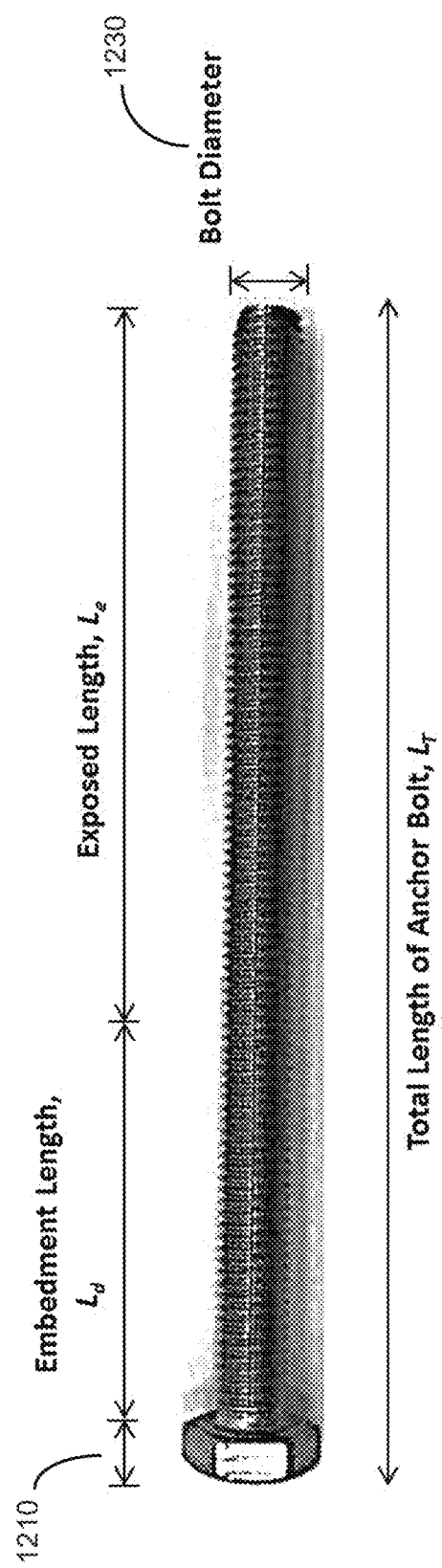
FIG. 12C is an illustrative view of an anchor bolt according to certain embodiments of the disclosure.

FIG. 12C is an illustrative view of an anchor bolt according to certain embodiments of the disclosure. In FIG. 12C, steel anchor bolts 1215 with diameter 1230 of 8 mm, 10 mm and 12 mm were used. The total length $L_t$ for 12 mm and 10 mm anchor bolt is about 150 mm, while for 8 mm anchor bolt the total length is about 125 mm. One third of the length, known as embedment length, $L_d$, may be embedded into the concrete cylinder prior to the casting of concrete and two-thirds of the total length was exposed, $L_e$, as shown in FIG. 12C. Each anchor bolt 1215 may be centered in the cylindrical mold and held in place with the help of wires. As discussed above, embedment depth may be adjusted using the guide wires 310. Mechanical vibration can be provided to the filled cylinder for 10 seconds.

Figure 13:
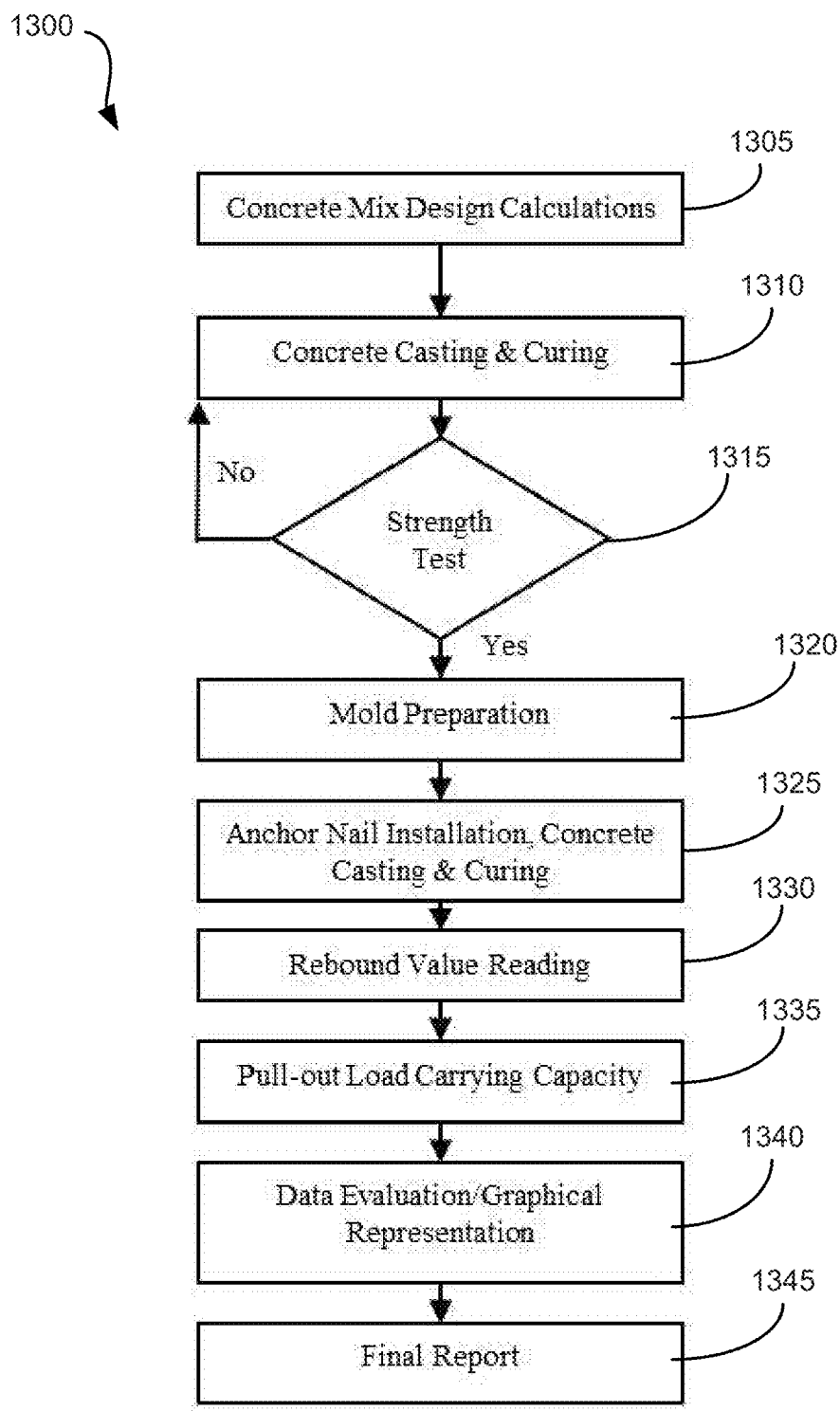
FIG. 13 is a flow chart of a method for determining the pull-out load carrying capacity of an anchor bolt according to certain embodiments of the disclosure.
Figure 15B:
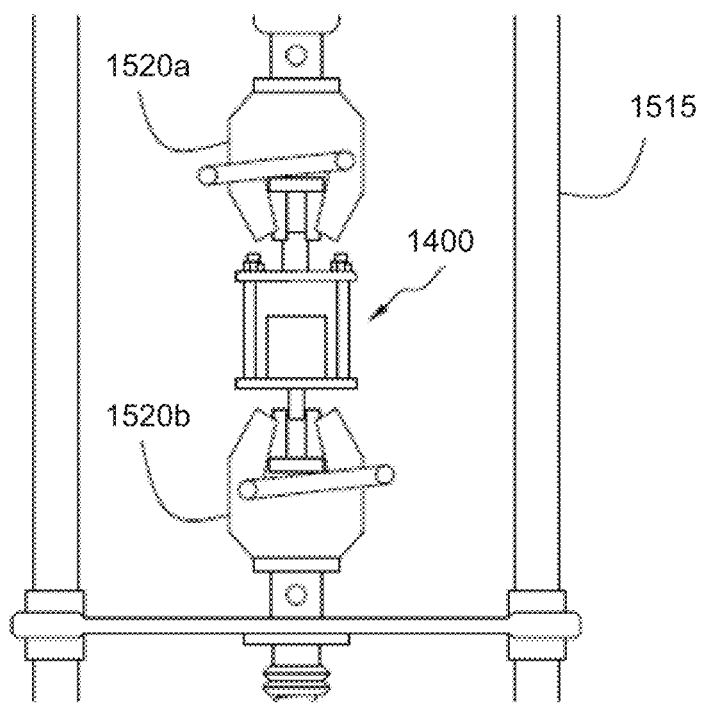
FIG. 15B is a partial schematic view of the UTM of FIG. 15A including the anchor cage assembly of FIGS. 14A and 14B mounted therein according to certain embodiments of the disclosure.

FIG. 13 is a flow chart of a method 1300 for determining the pull-out load carrying capacity of an anchor bolt according to certain embodiments of the disclosure. In FIG. 13, at 1305 concrete mix design calculations may be performed via controller 105. At 1310 concrete casting may be done to finalize the design mix. At 1315, the casting of normal strength concrete specimens may be concluded in three layers of equal thickness to ensure strength. At 1320, molding preparation may be performed to create the concrete specimens 1205. At 1325, anchor bolts may be inserted in empty concrete cylinders and held in place with the help of guide wires 310. These guide wires 310 may be temporarily installed to adjust the alignment and embedment length, $L_d$ of the anchor bolts 1215 prior to casting of concrete as shown in FIG. 3. Wires 310 may be removed upon demolding of the cylinders. Each filled concrete cylinder 1205 with installed anchor bolt 1215 may be mechanically vibrated for 10 seconds to complete the compaction process and levelled with the help of trowel taking care of the alignment of anchor bolts. Curing of the specimen was done in water tank for 28 days. FIG. 12A depicts the final specimens prior to testing. At 1330, rebound value readings are performed on each anchor bolt 1215. After rebound testing on bolts, concrete cylinder was inserted in the anchor cage and the completed assembly was placed in the hydraulic jacks of Universal Testing Machine (UTM) 1500 as shown in FIG. 15B.

At 1335, UTM 1500 may be employed for recording the pull-out load carrying capacity. At 1340, a detailed analysis of the results produced by the experimentation may be carried-out to identify the misaligned readings. Several key observations may be recorded during the data collection stage. At 1345, a report may be generated of the data. For example, a report may show that concrete compaction and placement around the anchor bolt may have a profound effect on each rebound value, R. Also, specimen with poor compaction of concrete around the anchor bolt may result in a lower rebound value, whereas specimen with proper compaction may result in higher rebound values.

FIG. 14A is a schematic perspective view of an anchor cage assembly 1400 including a concrete sample 1205 according to certain embodiments of the disclosure. In FIG. 14A, anchor cage assembly 1400 includes a reaction rod 1405, a first metal support plate 1410, a plurality of bracing rods 1415, a specimen 1205, an anchor 1215, and a second metal support plate 1420.

In some embodiments the first metal support plate 1410 and the second metal support plate 1420 are comprised of high strength steel or the like to withstand the tensile forces applied to the anchor 1215. Anchor 1215 may be configured as a bolt, rod or bar and embedded within specimen 1205. Specimen 1205 may comprise various forms of reinforced concrete, such as that found in various support structures, for example, garage floors, and other building structures. Also, specimen 1205 may be configured as a cylinder to be mounted within anchor cage assembly 1400 at the second metal support plate 1420, as shown in FIGS. 14A and 14B.

Reaction rod 1405 may comprise a high strength steel rod or bar welded to the first metal support plate 1410. The plurality of bracing rods 1415 may include a number of spaced-apart metal rods comprised of high strength steel welded at their distal ends to the second metal support plate 1420 and having screw threaded proximal ends with bolted on nuts above and below the plane of the first metal support plate 1410. Thus, the first metal support plate 1410 is configured to be removable from anchor cage assembly 1400. Alternatively, second metal support plate 1420 may be similarly configured to be removable from anchor cage assembly 1400. Further, first and second metal support plates 1410, 1420 are arranged in parallel planes to each other in exemplary embodiments. Also, in some embodiments, first and second metal support plates 1410, 1420 may be configured to be fixed to the plurality of bracing rods 1415 via welds or via bolted on nuts.

In FIG. 14A, the anchor cage assembly 1400 may be configured such that, for example, the reaction rod 1405 diametrically measures at or about 25 mm, the bracing rods 1415 diametrically measure at or about 25 mm, the first and second metal support plates 1410, 1420 diametrically measure at or about 300 mm with a thickness in the axial direction of the bracing rods 1415 of at or about 25 mm, and the specimen 1405 diametrically measures at or about 150 mm across and measures at or about 300 mm in an axial direction. These dimensions may provide maximum rigidity of anchor cage assembly 1400 while minimizing the amount and cost of materials used during testing. In some embodiments, the thicknesses of the first and second metal support plates 1410, 1420 may be configured such that the first metal support plate 1410 is thicker in an axial direction than the second metal support plate 1420 to provide increased strength when apparatus 1400 is placed under tension during a pull-out test.

Figure 14B:
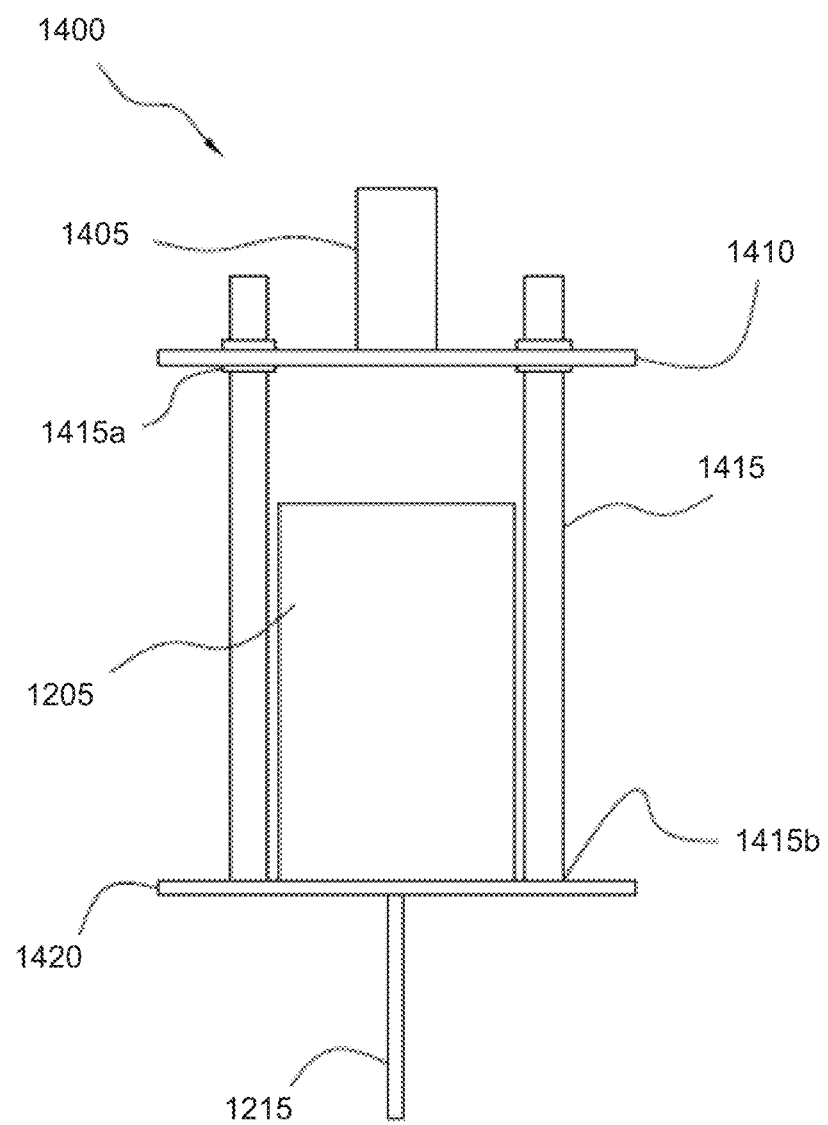
FIG. 14B is a schematic plan view of the anchor cage assembly including a concrete sample according to certain embodiments of the disclosure.

FIG. 14B is a schematic plan view of the anchor cage assembly 1400 including a concrete sample 1205 according to certain embodiments of the disclosure. In FIG. 14B, the plurality of bracing rods 1415 are shown in relation to the reaction rod 1405, the second metal support plate 1420 and the concrete cylinder specimen 1205. It should be noted that the second metal support plate 1420, the concrete cylinder specimen 1205 and the reaction rod 1405 are coaxially arranged in the anchor cage assembly 1400 to more evenly distribute tensile forces during testing. Further, in FIG. 14B, the plurality of bracing rods 1415 are shown to be six rods, however, a configuration of at least two rods may suffice based on the amount of tensile forces to be applied to the specimen during testing.

In some embodiments, the bracing rods 1415 may diametrically measure at or about 25 millimeters (mm), the anchor 1215 may diametrically measures at or about 20 with a maximum of 25 mm, the first and second steel support plates 1410, 1420 may diametrically measure at or about 300 mm, and the specimen 1205 may diametrically measures at or about 150 mm, for example. These dimensions may provide maximum rigidity of anchor cage assembly 1400 while minimizing the amount and cost of materials used during testing. Of course, other proportionally related dimensions may be used depending on the tests to be run and the materials comprising the specimen 1205 and the anchor 1215. Furthermore, second metal support plate 1420 includes an opening having a diameter at or about 30 mm, the opening being configured to allow the embedded anchor 1215 to pass there through.

In FIG. 14B, anchor cage assembly 1400 includes a pair of mounting nuts 1415 a screwed onto the proximal ends of each of the plurality of bracing rods 215 at locations immediately above and below the first metal support plate 1410. Further, the plurality of bracing rods 215 are welded at 1415b to the second metal support plate 1420. Weld 1415b coincides with the distal ends of the plurality of bracing rods 215. In this configuration, the first metal support plate 1410 may be removable and/or replaceable in order to accommodate different configurations or changes in the sample specimen's size or material as well as accommodating any different spaced bracing rod configurations.

FIG. 15A is a schematic view of a universal testing machine (UTM) 1500 according to certain embodiments of the disclosure. In FIG. 15A, the UTM 1500 includes a first crosshead 1505, a load cell 1510, support columns 1515, a first grip 1520a, a second grip 1520b, a second crosshead 1525, a recirculating ball screw system 1530, a protective sleeve 1535, a gearbox 1540, a DC/AC servomotor 1545, a base support 1550, and a control system 1555.

In certain embodiments, the first and second crossheads 1505, 1525 may be configured as movable members controlled to move up or down, usually at a constant speed. Some universal testing machines may program the crosshead speed or conduct cyclical testing, testing at constant force, testing at constant deformation, etc. Further, electro-mechanical, servo-hydraulic, linear drives, and resonance drives may be used. Load cell 1510 is a force transducer or the like configured to measure an applied load. Load cell 1510 may require period calibration to maintain its accuracy. Support columns 1515, often referred to as the load frame, may consist of two strong supports for the UTM 1500. First grip 1520a and second grip 1520b may be configured as tensile test grips or specimen holding jaws for performing a tensile test or the like.

FIG. 15B is a partial schematic view of the universal testing machine (UTM) 1500 of FIG. 15A showing the anchor cage assembly 1400 of FIGS. 14A and 14B mounted therein according to certain embodiments of the disclosure. In FIG. 15B, the anchor cage assembly 1400 is securely mounted between grips 1520a and 1520b to perform a tensile test via the UTM 1500. In this embodiment, reaction rod 1405 is mounted in grip 1520a and anchor 225 is mounted in grip 1520b. When an operator activates the control system 1555 for tensile testing, grip 1520a may remain fixed while grip 1520b may be configured to move away from grip 1520a via the movement of the second crosshead 1525 in an opposing direction to first crosshead 1505. As the grips 1520a and 1520b move farther apart load cell 1510 is configured to measure the applied load via force transducers (not shown) while the control system 1555 records the load data and the displacement data during each test until anchor 225 is pulled out of specimen 1205 or any other test constraints or conditions are met. Alternatively, grip 1520a may be configured to move while grip 1520b remains fixed or both grips 1520a, 1520b may be configured to move in opposing directions. DC/AC servomotor 1545 is configured to cause gearbox 1540 to rotate a drive belt which in turn causes the recirculating ball screw system 1530 to move crosshead 1525 up or down along support columns 1515 during operation, thereby moving grip 1520b.

Anchor cage assembly 1400 as shown in FIGS. 14A and 14B and a universal testing machine (UTM) 1500 as shown in FIGS. 15A and 15B can be configured, for example, to conduct anchor pull-out strength testing of specimens. Traditionally, such testing requires a hydraulic jack, pressure gauge, data acquisition system (DAS), data storage and management system (DSMS), LVDT and specialized manpower. However, using the anchor cage assembly 1400 coupled with the UTM 1500, the above mentioned traditional equipment can be replaced and the laboratory pull-out strength testing for concrete anchor bars and anchor bolts can be made time and cost effective, efficient and will not require specialized labor. Furthermore, by utilizing the data acquisition, management and storage system embedded in the UTM 1500, the need of separate data storage and management device can be eradicated and real-time displacement verses strength graph can be obtained.

Anchor cage assembly 1400 can be used to carry out pull-out testing of an anchor rod/bar 1215 using the universal testing machine 1500 whereas traditional testing practice is to use an assembly of hydraulic jack, reaction frame, load cells and data acquisition system, which is expensive to setup and requires skilled labor. On the other hand, using the anchor cage assembly 1400 of the present disclosure will result in a simple setup without the need for a complex reaction frame, load cell, hydraulic jack and data acquisition system, which will lead to a much more economical pull-out test. Further, the anchor cage assembly 1400 results in a non-destructive test to evaluate the load carrying capacity of the anchor rod/bar 1215.

Figure 16:
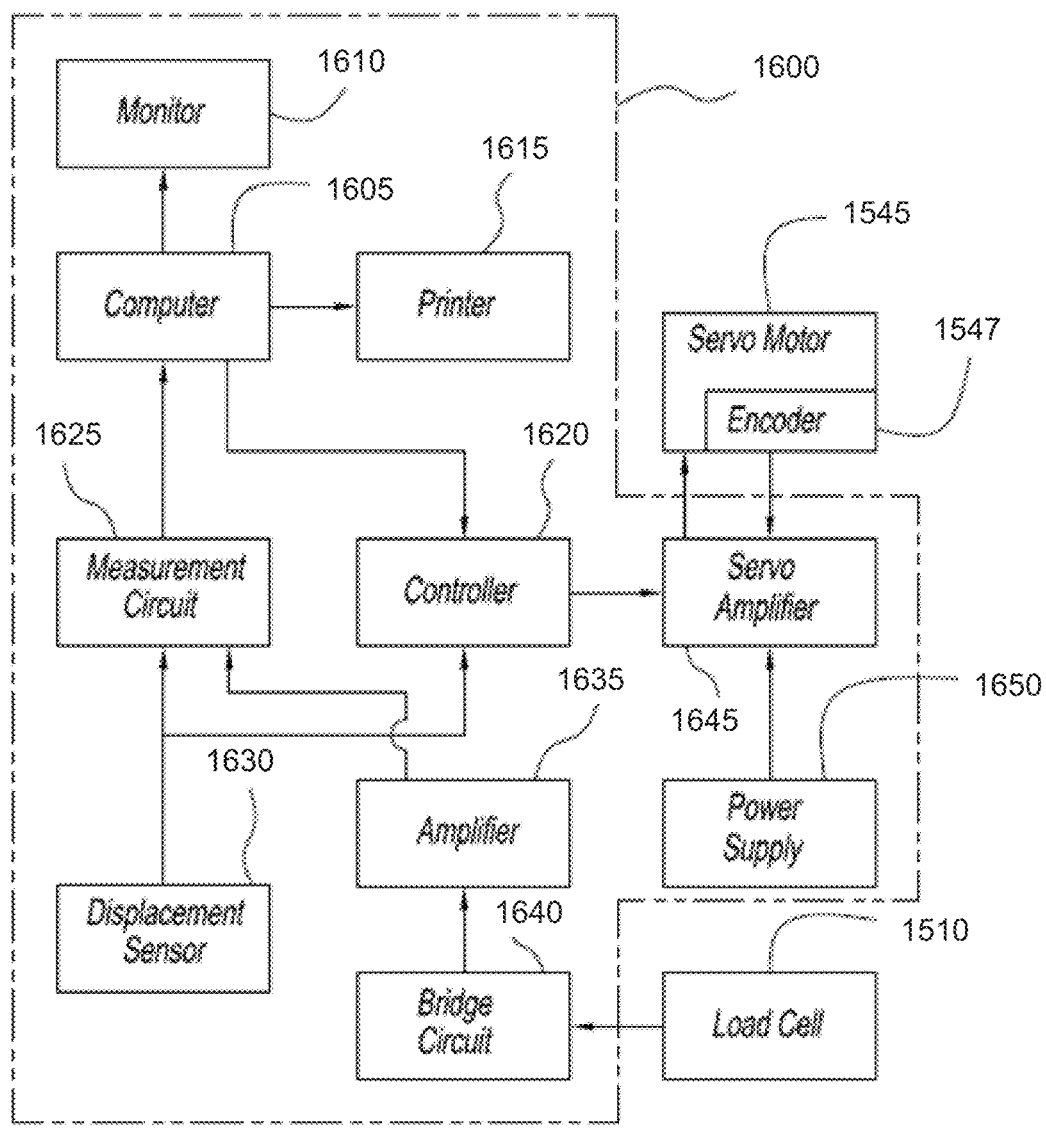
FIG. 16 is a block diagram of a control system for the UTM according to certain embodiments of the disclosure.

FIG. 16 is a block diagram of a control system 1600 for the universal testing machine (UTM) 1500 according to certain embodiments of the disclosure. In FIG. 16, the control system 400 (similar to control system 1555 of FIG. 15A) includes a computer 1605, a monitor 1610, a printer 1615, a controller 1620, a measuring circuit 1625, a displacement sensor 1630, an amplifier 1635, a bridge circuit 1640, a servo amplifier 1645, and a power supply 1650. In some embodiments, the load cell 1510 and the DC servomotor 1545 having an encoder 1537 are connected to the control system 1600.

In some embodiments, the control system 1600 of the UTM 1500 performs the driving control and the measurement process of the UTM 1500. The servo amplifier 1645 generates a driving current for driving the DC servomotor 1535 from power supplied from the power supply 1650 based on a target speed signal sent from the controller 1620, and supplies the driving current to the servomotor 1535. An encoder 1537 for measuring the rotation speed of the servomotor 1535 is provided on a drive shaft of the servomotor 1535. The servo amplifier 1645 executes the feedback control in which the power (e.g., a pulse width of the driving current in the case of the pulse width modulation) to be supplied to the servomotor 1535 is adjusted based on the rotation speed of the drive shaft of the servomotor 1535. With this configuration, the servomotor 1535 is controlled so that the rotation speed of the drive shaft of the servomotor 1535 becomes equal to the target speed.

An output of the load cell 1510, which measures the load applied to the test piece, for example, the anchor bolt/bar 1215, is input to the measurement circuit 1625 via the bridge circuit 1640 and the amplifier 1635. Similarly, an output of the displacement sensor 1630 for measuring the displacement of the test piece is input to the measurement circuit 1625. The measurement circuit 1625 executes an A-D conversion for the analog signals from the load cell 1510 and the displacement sensor 1630, and transmits the converted signals to the computer 1605. The displacement sensor 1630 may include a linear variable displacement transducer (LVDT) or the like.

The computer 1605 is configured to plot a graph based on the load and displacement transmitted from the measurement circuit 1625, and displays it on the monitor 1610. For example, the computer 1605 calculates the stress applied to the test piece from the measurement value of the load and the sectional area of the test piece which has been measured in advance, and calculates the distortion of the test piece from the measurement value of the displacement and the size (actually, the distance between the chucks) of the test piece in the applying direction of the load. Then, the computer 1605 displays the plot of the stress-distortion curve in real-time. The computer 1605 is also able to print out the plotted graph via printer 1615.

By operating the computer 1605, an operator of the universal testing machine 1500 transmits an indication value of the moving speed of the second crosshead 1525 to the controller 1620. Based on the indication value of the moving speed and the displacement sent from the displacement sensor 1630, the controller 1620 calculates the target speed signal to be sent to the servo amplifier 1645, and transmits the target speed signal to the servo amplifier 1645. The displacement is measured from a predetermined datum which is recorded and stored by the computer 1605.

Currently there are several built-to-purpose machines available in the market which can be employed to do the pull-out testing. However, using the developed anchor cage assembly 1400 in combination with UTM 1500 as shown in FIG. 15B pull-out load testing may be easily performed, thereby eradicating the need to purchase new expensive equipment for conducting pull-out testing. All the results presented in the current research are obtained using the experimental setup as shown in FIGS. 15A and 15B. This novel innovation not only resulted in reducing the cost of testing but also eradicated the need of a complex test setup requiring load cell, data acquisition system and LVDT. In addition, the anchor cage assembly 1400 can be used with any model of universal testing machine (UTM) and effectively diminishes the need of separate pull-out testing equipment for lab testing purposes.

Figure 17:
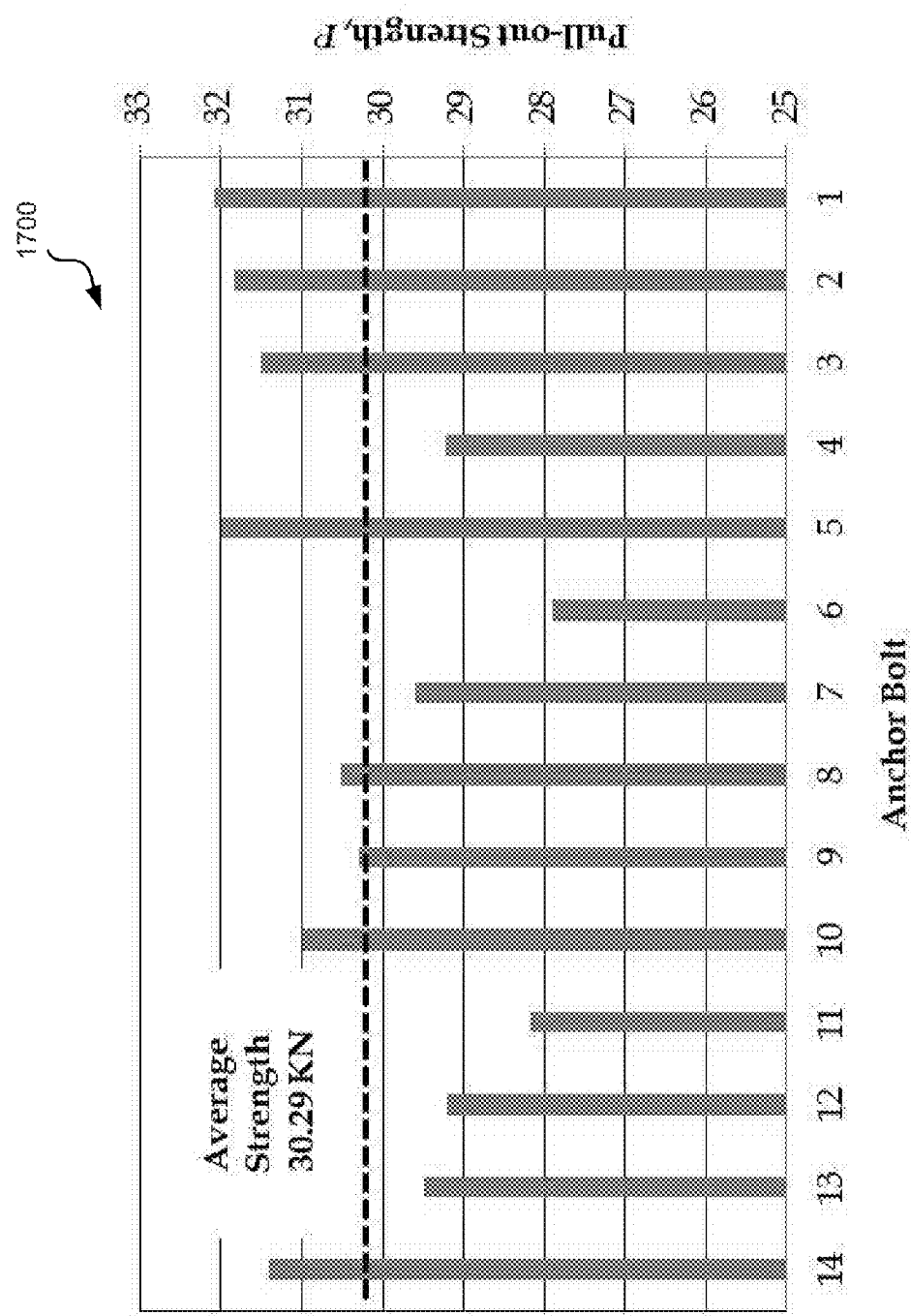
FIG. 17 is a bar graph illustrating a variation in pull-out load strength for an 8 mm diameter anchor bolt with a 50 mm embedment length according to certain embodiments of the disclosure.

FIG. 17 is a bar graph 1700 illustrating a variation in pull-out load strength for an 8 mm diameter anchor bolt with a 50 mm embedment length according to certain embodiments of the disclosure. For instance, the average pull-out strength for a 8 mm diameter anchor bolt with a 50 mm embedment length may be calculated, for example 30.29 KN average strength.

Figure 18:
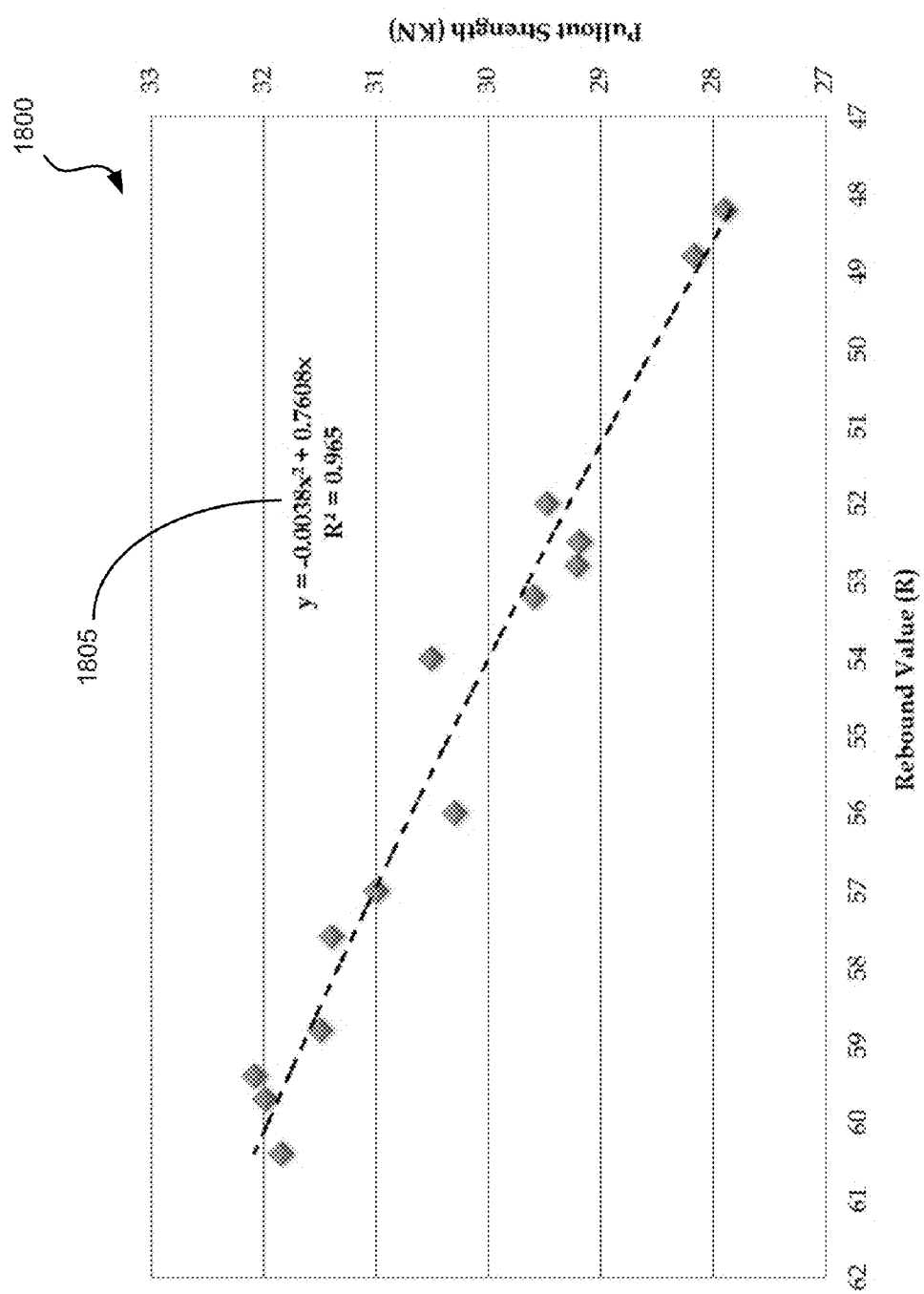
FIG. 18 is a graphical plot of rebound value verses pull-out strength for an 8 mm diameter anchor bolt with a 50 mm embedment length according to certain embodiments of the disclosure.

FIG. 18 is a graphical plot 1800 illustrating rebound value verses pull-out strength for an 8 mm diameter anchor bolt with a 50 mm embedment length according to certain embodiments of the disclosure. In FIG. 18, certain embodiments show a clear mathematical relationship 1805 between the rebound value, R and the pull-out load capacity, P of $y=0.0036x^2+0.3654x$ for a 8 mm diameter bolt with a 50 mm embedment length in concrete, where x is the rebound value and y is the estimated pull-out strength.

It can be seen that as the rebound value, R increases the pull-out load capacity also increases, however there exists a clear range starting from 45 to the peak value at 60. The anchors with-in this range attains a good load carrying capacity. It is worth mentioning here that the anchor load capacity depends on embedment length, alignment and nature of surrounding material. Hence the anchor with pull-out values at the lower end of the range represent slight misalignment, less than 5° and were embedded in concrete which had pores owing to improper compaction. Hence it can be concluded from the presented result and above mentioned discussion that rebound value R of 45 can be treated as a cut-off point for 8 mm anchor bolts with embedment length of 50 mm embedded in normal strength concrete. Rebound value below this represents improper installation, poor quality of concrete which cannot be relied upon for good pull-out load capacity. Further, Table 1 shows the rebound values and pull-out load values for FIG. 18.

TABLE 1

Relationship between Pull-out Strength and Rebound Value for 8 mm Diameter Bolt with embedment length 50 mm

| Bolt No. | Rebound Value (R) | | | | | Average value (R) | Pull-out Strength (KN) | Comments |
|---|---|---|---|---|---|---|---|---|
| | 1 | 2 | 3 | 4 | 5 | | | |
| 1 | 54 | 71 | 58 | 56 | 58 | 59.4 | 32.08 | V |
| 2 | 53 | 65 | 65 | 55 | 64 | 60.4 | 31.84 | V |
| 3 | 60 | 55 | 59 | 59 | 61 | 58.8 | 31.5 | V |
| 4 | 47 | 53 | 50 | 57 | 57 | 52.8 | 29.21 | V |
| 5 | 61 | 60 | 64 | 54 | — | 59.7 | 31.99 | V |
| 6 | 40 | 47 | 56 | 51 | 47 | 48.2 | 27.9 | V |
| 7 | 56 | 50 | 55 | 51 | — | 53.2 | 29.6 | V |
| 8 | 45 | 51 | 55 | 64 | 55 | 54 | 30.51 | Bolt Failure |
| 9 | — | 47 | — | — | — | — | — | NV (20°) |
| 10 | 47 | 59 | 54 | 64 | — | 56 | 30.3 | NV (5°) |
| 11 | 55 | 52 | 51 | 60 | 66 | 57 | 31 | V |
| 12 | 44 | 54 | 56 | 48 | 42 | 48.8 | 28.17 | V |
| 13 | 56 | 53 | — | 60 | 41 | 52.5 | 29.19 | V |
| 14 | — | 50 | 56 | 55 | 47 | 52 | 29.48 | V |
| 15 | 53 | 56 | 59 | 57 | 63 | 57.6 | 31.4 | V |

Figure 19:
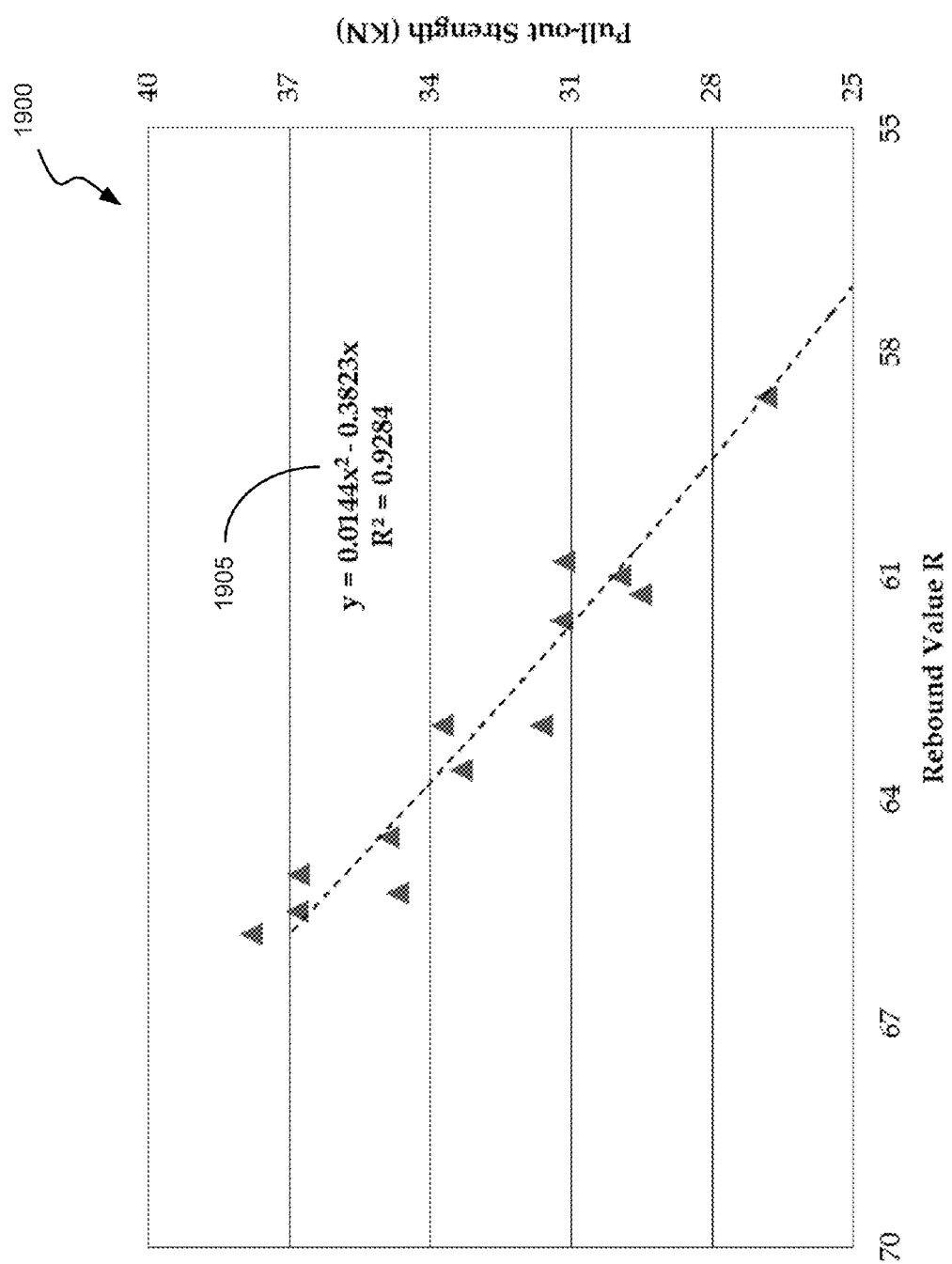
FIG. 19 is a graphical plot of rebound value verses pull-out strength for a 10 mm diameter anchor bolt with a 50 mm embedment length according to certain embodiments of the disclosure.

FIG. 19 is a graphical plot 1900 of rebound value verses pull-out strength for a 10 mm diameter anchor bolt with a 50 mm embedment length according to certain embodiments of the disclosure. In FIG. 19, certain embodiments show a clear mathematical relationship 1905 between the rebound value, R and the pull-out load capacity, P of $y=-0.0038x^2+0.7608x$ for a 10 mm diameter bolt with a 50 mm embedment length in concrete, where x is the rebound value and y is the estimated pull-out strength.

However the range of rebound value and pull-out capacity is slightly higher than the 8 mm bolt. This fact can be attributed to the explanation that since the larger diameter bolt has a larger surface area, it has a stronger bond with the surrounding concrete hence is better able to carry load and transmit impact loading. From Table 2 it can be seen that the inclined anchor show a lower load carrying capacity owing to poor installation and quality of surrounding concrete. Hence the rebound value R of 60 can be treated as the a cut-off point for 10 mm anchor bolts with embedment length of 50 mm embedded in normal strength concrete. FIG. 19 depicts the pull-out load carrying capacity versus the rebound value relationship for the 10 mm diameter anchor bolts, embedded 50 mm into normal strength concrete. Table 2 shows the rebound value and pull-out load value for FIG. 19.

TABLE 2

Relationship between Pull-out Strength and Rebound Value for 10 mm Diameter Bolt with embedment length 50 mm

| Bolt No. | Rebound Value (R) | | | | | Average value (R) | Pull-out Strength (KN) | Comments |
|---|---|---|---|---|---|---|---|---|
| | 1 | 2 | 3 | 4 | 5 | | | |
| 1 | 70 | 67 | 64 | 62 | 52 | 63 | 33.74 | V |
| 2 | 64 | 70 | 63 | 63 | 69 | 65.8 | 37.8 | V |
| 3 | 67 | — | 62 | 66 | 67 | 65.5 | 36.83 | V |
| 4 | 58 | 49 | 59 | 62 | 65 | 58.6 | 26.85 | NV (10) |
| 5 | 57 | 63 | 60 | 61 | 63 | 60.8 | 31.14 | V |
| 6 | 65 | 64 | 63 | 71 | 62 | 65 | 36.8 | V |
| 7 | 55 | 67 | 68 | 68 | — | 64.5 | 34.88 | V |
| 8 | 57 | 68 | 61 | 63 | 66 | 63 | 31.63 | V |
| 9 | 55 | 62 | 51 | 70 | 67 | 61 | 29.95 | V |
| 10 | 53 | 65 | 65 | 62 | — | 61.25 | 29.52 | V |
| 11 | 59 | 55 | 59 | 67 | 68 | 61.6 | 31.2 | V |
| 12 | 59 | 67 | 67 | 61 | 67 | 64.2 | — | NV (15) |
| 13 | 60 | 67 | 70 | 64 | — | 65.25 | 34.7 | V |
| 14 | 50 | 47 | 54 | 60 | 50 | 52.2 | — | NV (20) |
| 15 | 57 | 60 | 67 | 65 | 69 | 63.6 | 33.33 | V |

Figure 20:
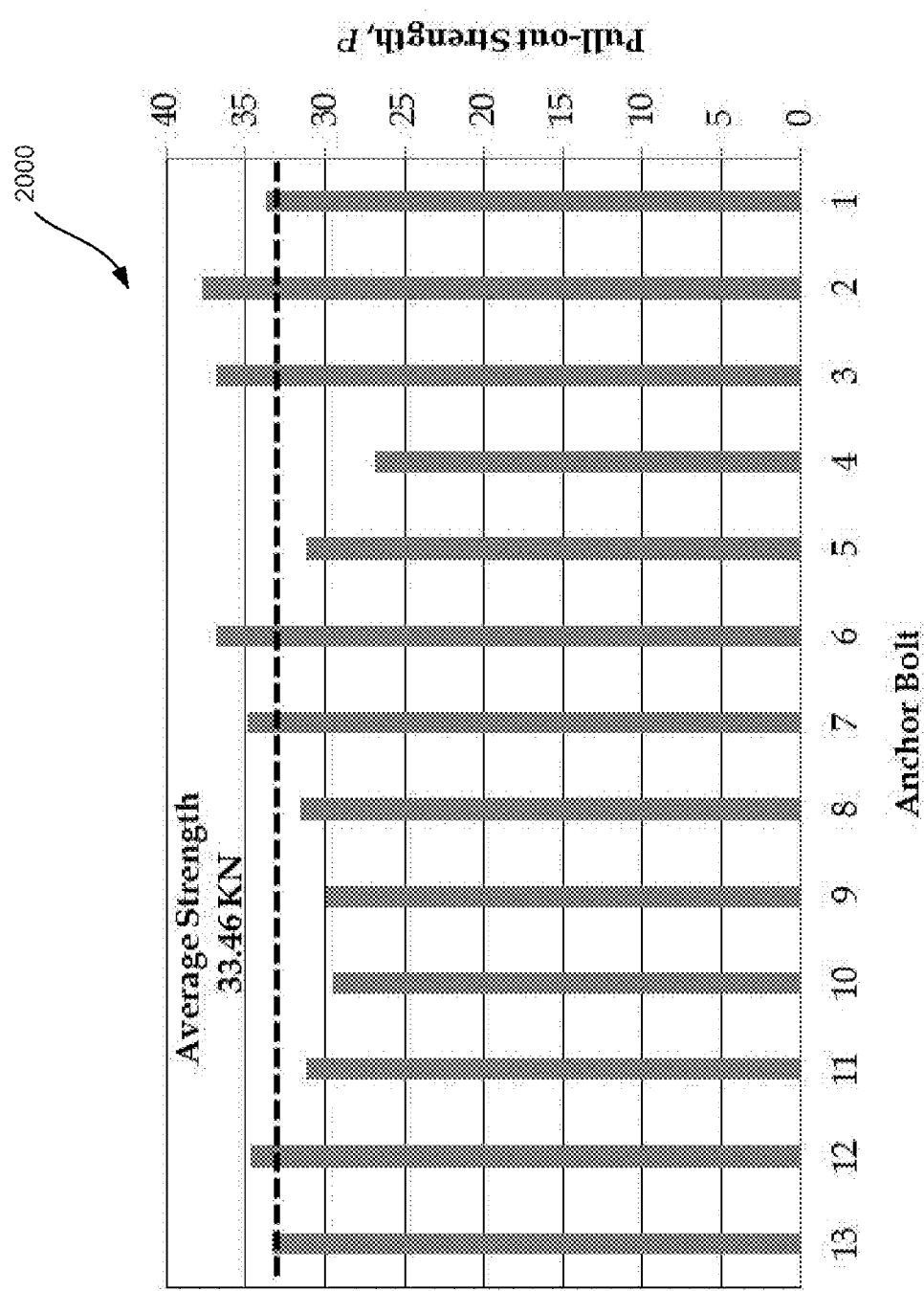
FIG. 20 is a bar graph illustrating a variation in pull-out load strength for a 10 mm diameter anchor bolt with a 50 mm embedment length according to certain embodiments of the disclosure.

FIG. 20 is a bar graph 2000 illustrating a variation in pull-out load strength for a 10 mm diameter anchor bolt with a 50 mm embedment length according to certain embodiments of the disclosure. For instance, the average pull-out strength for a 10 mm diameter anchor bolt with a 50 mm embedment length may be calculated, for example 33.46 KN average strength.

Figure 21:
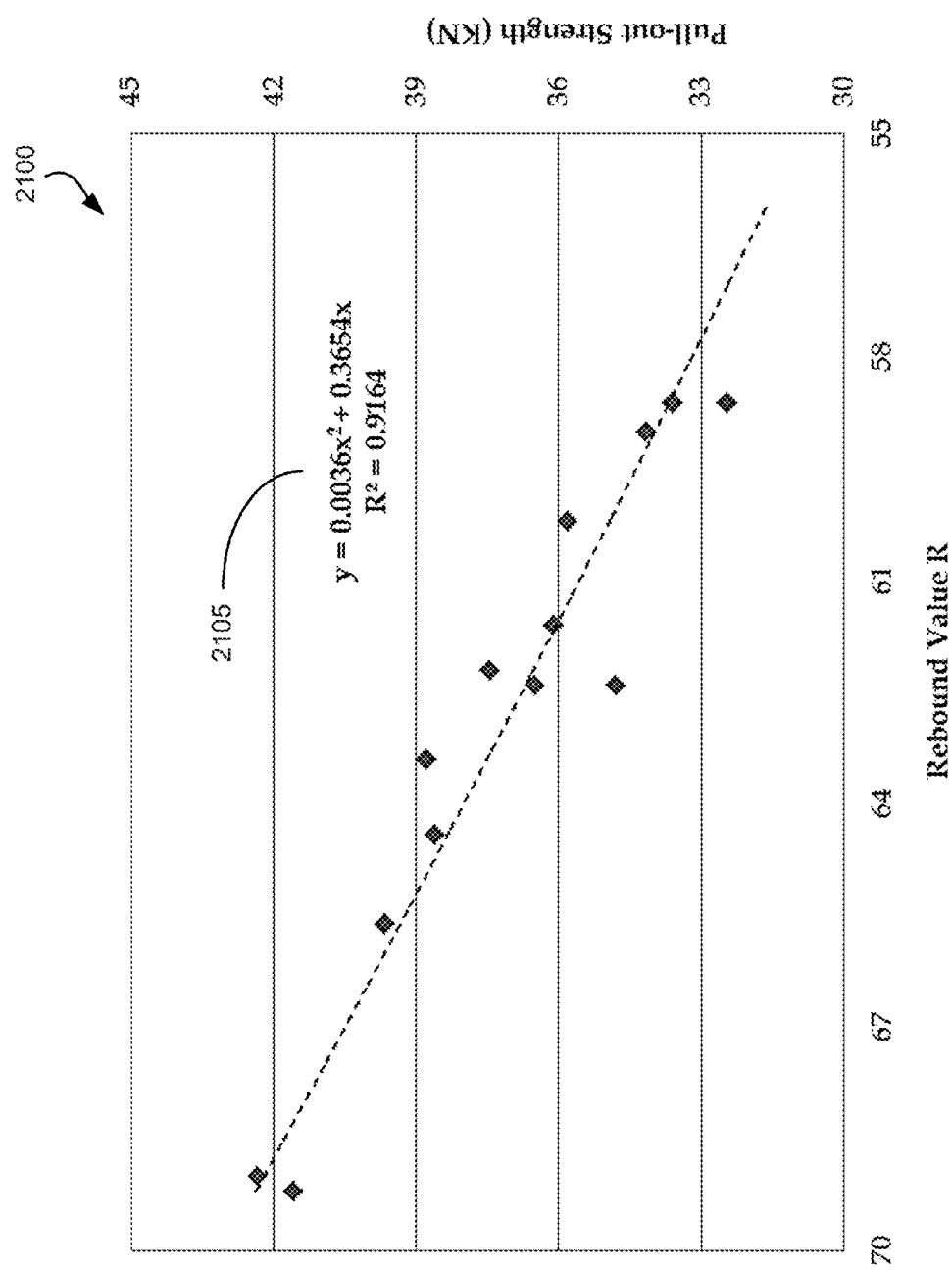
FIG. 21 is a graphical plot of rebound value verses pull-out strength for a 12 mm diameter anchor bolt with a 50 mm embedment length according to certain embodiments of the disclosure.

FIG. 21 is a graphical plot of rebound value verses pull-out strength for a 12 mm diameter anchor bolt with a 50 mm embedment length according to certain embodiments of the disclosure. In FIG. 21, certain embodiments show a clear mathematical relationship 2105 between the rebound value, R and the pull-out load capacity, P of $y=0.0144x^2-0.3823x$ for a 12 mm diameter bolt, where x is the rebound value and y is the estimated pull-out strength.

However, the range of rebound value and pull-out capacity is slightly higher than the 10 mm bolt. This fact can be attributed to the explanation as given above. From Table 3 it can be seen that the inclined anchor show a lower load carrying capacity owing to poor installation and quality of surrounding concrete. Hence the rebound value R of 60 can be treated as the a cut-off point for 12 mm anchor bolts with embedment length of 50 mm embedded in normal strength concrete. Rebound value below this represents improper installation which cannot be relied upon for larger pull-out load capacity. Table 3 shows the rebound value and pull-out load value for FIG. 21.

TABLE 3

Relationship between Pull-out Strength and Rebound Value for 12 mm Diameter Bolt with embedment length 50 mm

| Bolt No. | Rebound Value (R) | | | | | Average value (R) | Pull-out Strength (KN) | Comments |
|---|---|---|---|---|---|---|---|---|
| | 1 | 2 | 3 | 4 | 5 | | | |
| 1 | 69 | 69 | 73 | 70 | 64 | 69 | 42.33 | V |
| 2 | 61 | 60 | 71 | 69 | 67 | 65.6 | 39.67 | V |
| 3 | 67 | 66 | 56 | 57 | 49 | 59 | 34.16 | V |
| 4 | 62 | 61 | 54 | 65 | 59 | 60.2 | 35.81 | V |
| 5 | 68 | 57 | 53 | 57 | 51 | 57.2 | — | NV (20°) |
| 6 | 61 | 55 | 67 | 51 | 59 | 58.6 | 33.59 | V |
| 7 | 67 | 68 | 58 | 54 | 65 | 62.4 | 34.8 | NV (5°) |

TABLE 3-continued

Relationship between Pull-out Strength and Rebound Value
for 12 mm Diameter Bolt with embedment length 50 mm

| Bolt No. | Rebound Value (R) | | | | | Average value (R) | Pull-out Strength (KN) | Comments |
|---|---|---|---|---|---|---|---|---|
| | 1 | 2 | 3 | 4 | 5 | | | |
| 8 | 64 | 75 | 69 | 73 | 65 | 69.2 | 41.58 | V |
| 9 | 62 | 68 | 60 | 65 | 67 | 64.4 | 38.61 | V |
| 10 | 50 | 60 | 59 | 60 | 51 | 56 | — | NV (20°) |
| 11 | 54 | 60 | 65 | 69 | 69 | 63.4 | 38.79 | V |
| 12 | 58 | 58 | 62 | 64 | 66 | 61.6 | 36.1 | V |
| 13 | 53 | 70 | 62 | 61 | 66 | 62.4 | 36.5 | V |
| 14 | 58 | 49 | 54 | 67 | 65 | 58.6 | 32.46 | NV (5°) |
| 15 | 60 | 71 | 59 | 65 | 56 | 62.2 | 37.44 | V |

Figure 22:
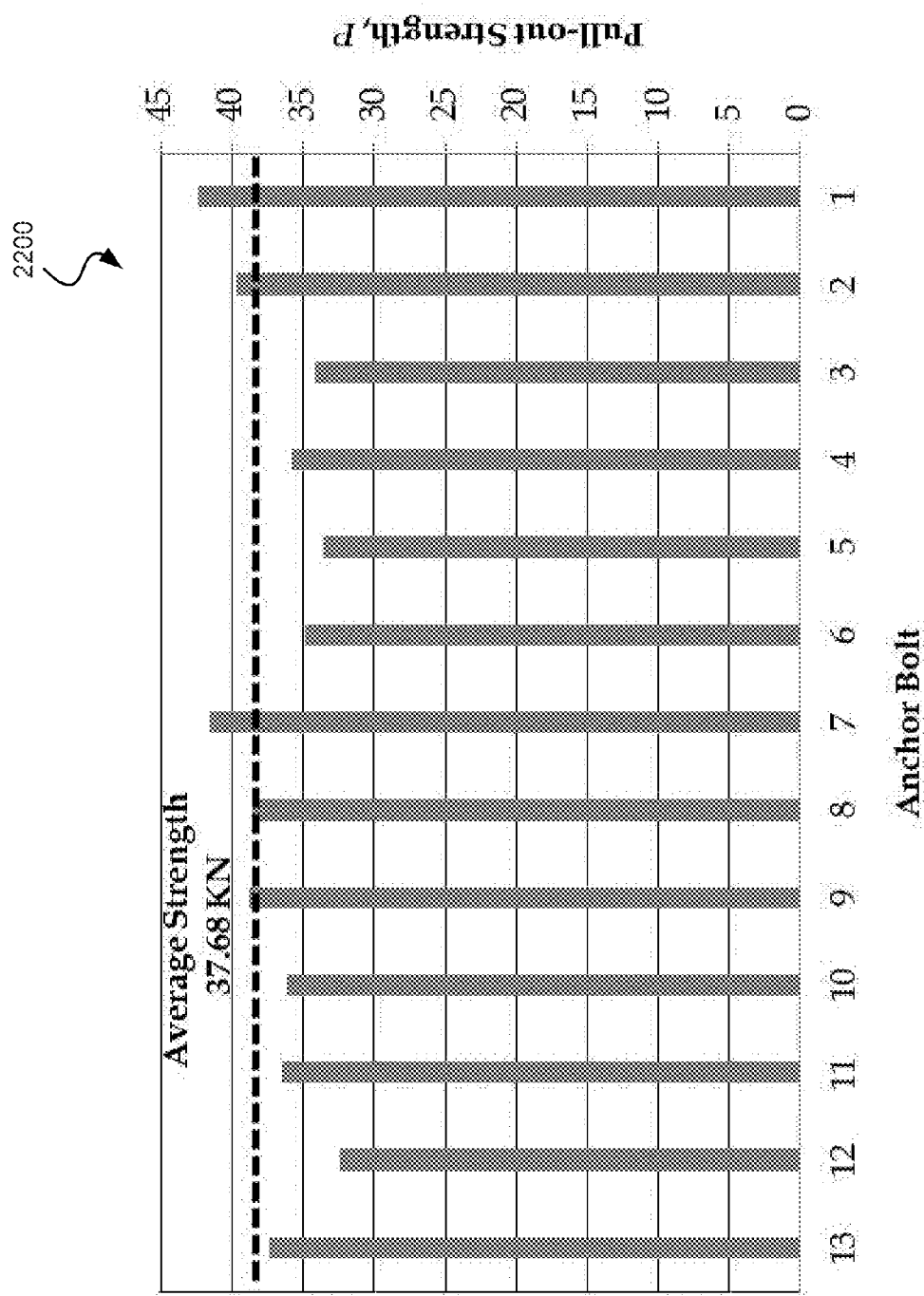
FIG. 22 is a bar graph illustrating a variation in pull-out load strength for a 12 mm diameter anchor bolt with a 50 mm embedment length according to certain embodiments of the disclosure.

FIG. 22 is a bar graph 2200 illustrating a variation in pull-out load strength for a 12 mm diameter anchor bolt with a 50 mm embedment length according to certain embodiments of the disclosure. For instance, the average pull-out strength for a 12 mm diameter anchor bolt with a 50 mm embedment length may be calculated, for example 37.68 KN average strength.

Figure 23:
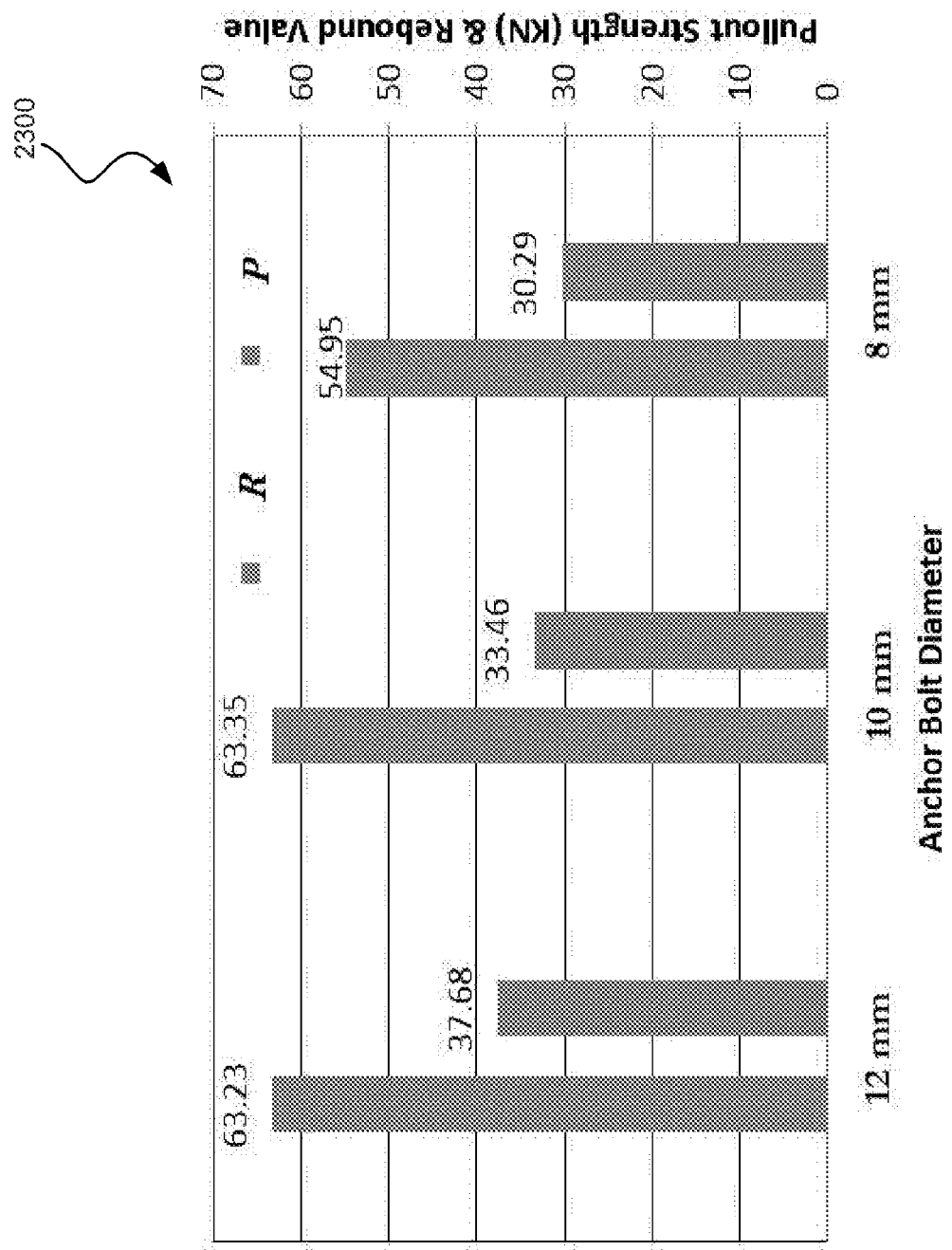
FIG. 23 is a bar graph illustrating an average rebound value and pull-out strength comparison according to certain embodiments of the disclosure.

FIG. 23 is a bar graph 2300 illustrating an average rebound value and pull-out strength comparison according to certain embodiments of the disclosure. In FIG. 23, 8 mm, 10 mm, and 12 mm diameter anchor bolts were aligned exactly vertically. The average rebound values, R of 10 mm and 12 mm diameter anchor bolts were almost at the same level at about 63 which is 13.2% greater than that in the 8 mm diameter bolts. However the maximum pull-out strength, P was noticed in 12 mm diameter bolt followed by 10 mm and 8 mm bolt, respectively. The maximum average pull-out strength was 37.68 KN which was 11.2% greater than 10 mm bolt and 19.6% greater than 8 mm bolts. While the difference in strength among 10 mm and 8 mm bolts was 8.4%. It can be seen from the result that even for same rebound value the pull-out value for larger diameter bolt is greater which is in agreement with the above explanation regarding bond performance.

Figure 24:
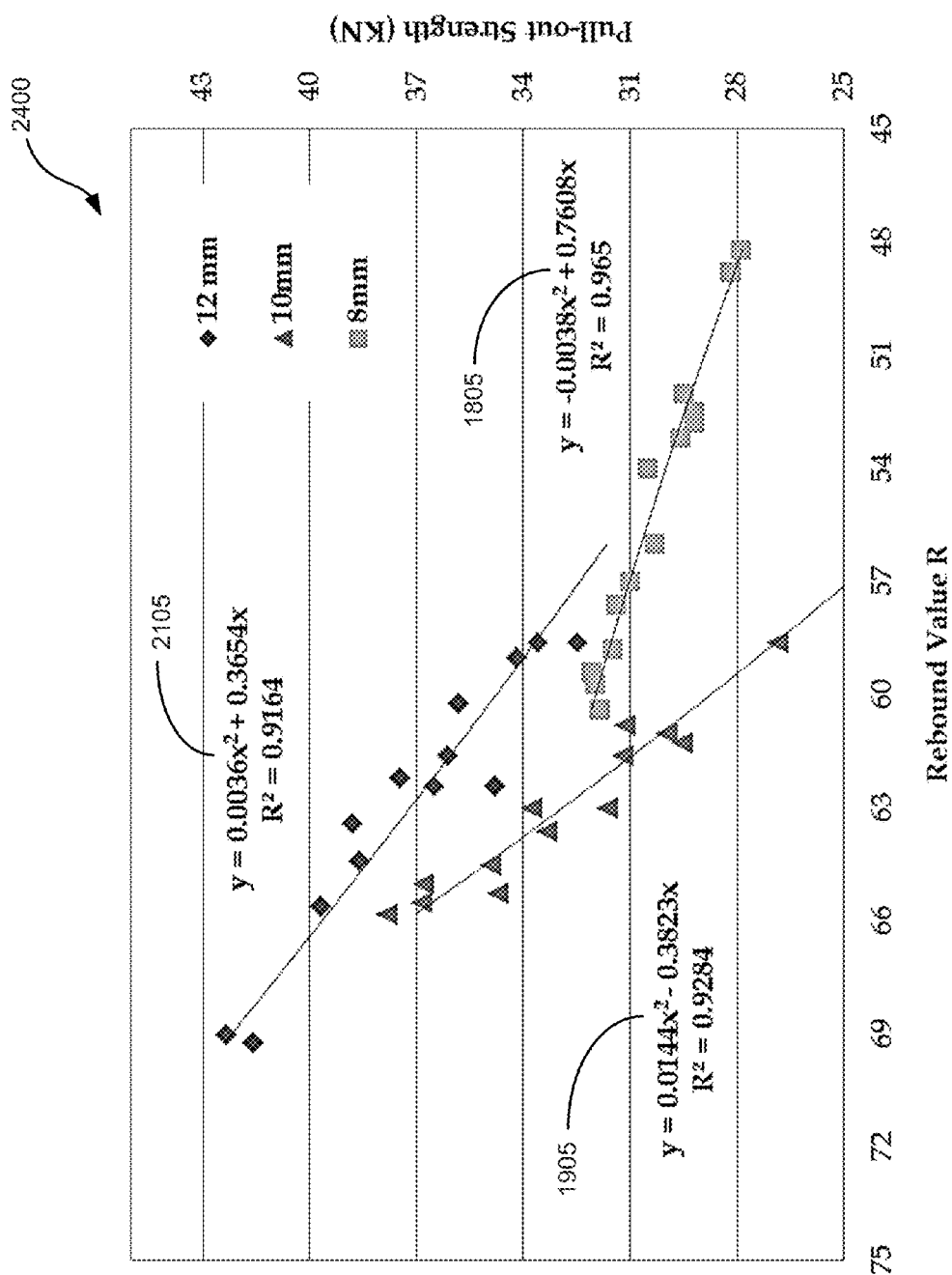
FIG. 24 is a graphical combined plot of rebound value verses pull-out strength for 8 mm, 10 mm, and 12 mm diameter anchor bolts as shown in FIGS. 17, 19, and 21 according to certain embodiments of the disclosure.

FIG. 24 is a graphical combined plot 2400 of rebound value verses pull-out strength for 8 mm, 10 mm, and 12 mm diameter anchor bolts as shown in FIGS. 18, 19 and 21 according to certain embodiments of the disclosure. FIG. 24 depicts the pull-out load carrying capacity versus the rebound value relationship at 1805, 1905, and 2105 for the 8 mm, 10 mm and 12 mm diameter anchor bolt, respectively, each embedded 50 mm into normal strength concrete.

It can be seen from the above disclosure that there exist clear boundaries depending upon the diameter of the anchor bolt. Larger diameter bolt is able to carry the larger pull-out load, however it is important to note that for 10 mm and 12 mm anchor bolts the range of rebound value R begins at same level but continues to a larger value for 12 mm bolts. Also, it can be seen that with gradual increase in anchor bolt diameter the load carrying capacity increases in overlapping zones. The lower end of larger diameter anchor overlaps with the higher end of lower diameter anchor bolt. Also, it is evident that inclined (non-vertical) anchor bolts, bolts embedded in porous concrete and bolts with improper embedment length can be identified using the disclosed relationships as the resulting pull-out load capacities, P are lower and the rebound values, R lie outside the specified zone for the particular diameter anchor bolts.

Figure 25:
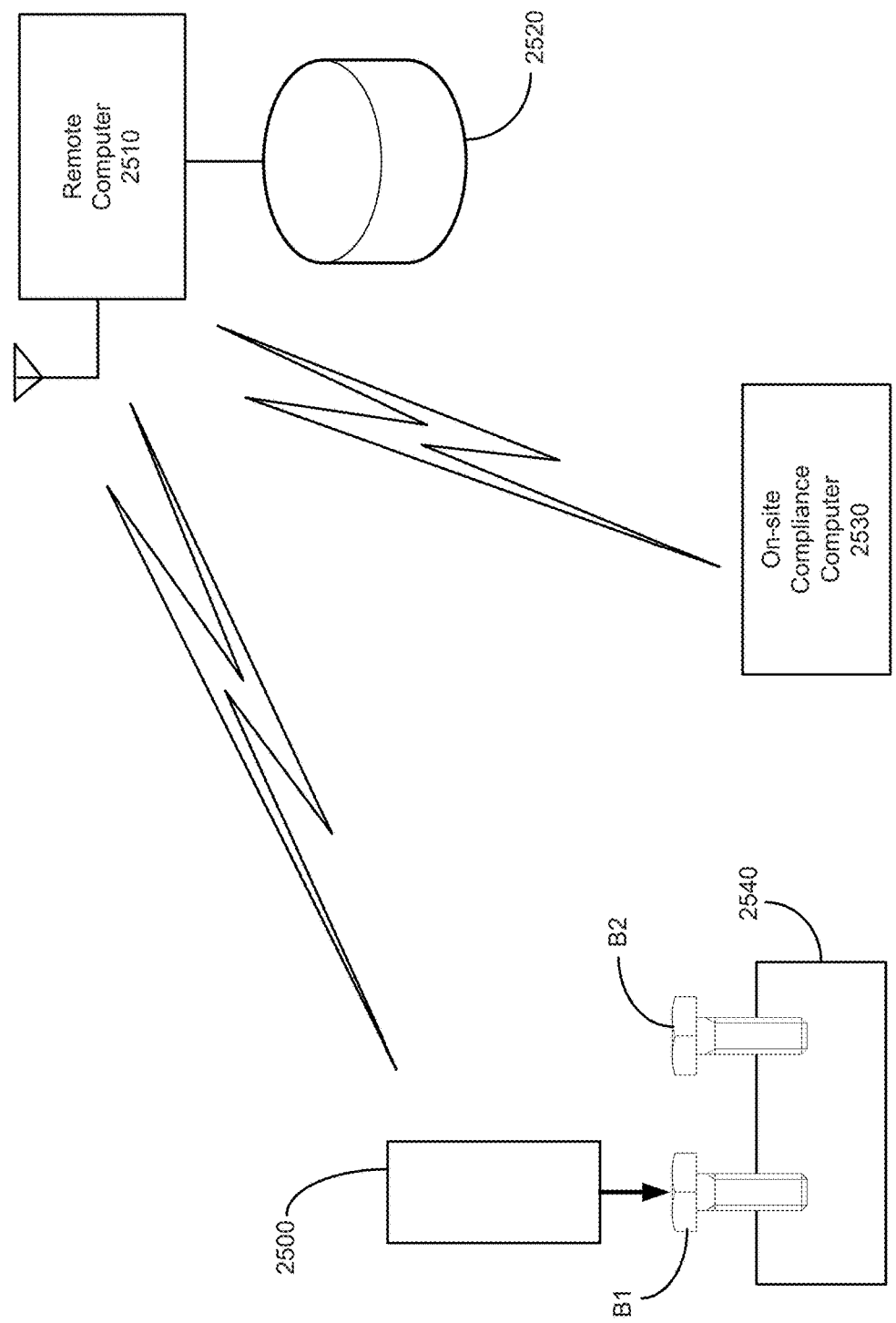
FIG. 25 is a system of a diagram of a Schmidt hammer that is used to measure a pull-out strength of respective anchor bolts in a construction project according to certain embodiments of the disclosure.

FIG. 25 is a system of a diagram of a Schmidt hammer 2500 that is used to measure a pull-out strength of respective anchor bolts in concrete 2540 of a construction project according to certain embodiments of the disclosure. In FIG. 25, the Schmidt hammer 2500 when testing anchor bolt B1 prepares a message that identifies the location of the Schmidt hammer 2500 at anchor bolt B1 (determined through triangulation and GPS location as discussed above), anchor bolt ID, and Schmidt hammer measurement. The message packet in this example is transmitted wirelessly to a remote computer 2510 that receives the packet and compares the Schmidt hammer measurement to a pull-out strength analysis model so as to identify the pull-out strength for anchor bolt B1. The pull-out strength is then compared to specification requirements stored in the database 2520 to determine whether the measured (estimated) pull-out strength of anchor bolt B1 is at or above the specified requirement as saved in the database 2520. The conclusion of the compliance analysis is transmitted from the remote computer 2510 to the on-site compliance computer 2530 so that if directive action needs to be taken on anchor bolt B1 (perhaps through reinstallation), corrective action may be taken shortly after the installation of anchor bolt B1. On the other hand, if the measurement indicates that the pull-out strength of anchor bolt B1 surpasses that of the requirement, then a compliance flag is saved in association with the recorded measurement for anchor bolt B1.

The process then repeats where the Schmidt hammer 2500 is used to measure the pull-out strength of anchor bolt B2. This process continues throughout all of the anchor bolts on a construction job so that after all the anchor bolts have been tested, a real-time compliance report may be prepared and saved at the database 2520. Also, an on-site repair report may be generated for the different anchor bolts that fail to meet or exceed the pull-out requirements that were previously set in the database 2520.

The remote computer 2510 need not be located on a construction site, but may rather be located at a central facility such that a service may be provided for rapid compliance analysis performed for a construction job. A benefit associated with this approach is that no special skill is needed for performing the compliance testing by the operator of the Schmidt hammer 2500. Also, real-time reports and corrective action may be taken by associating the Schmidt hammer measurement results with the analytical model to predict the pull-out strength through the anchor bolts, and then comparing those predicted pull-out strengths to required pull-out strengths for the construction job.

Figure 26:
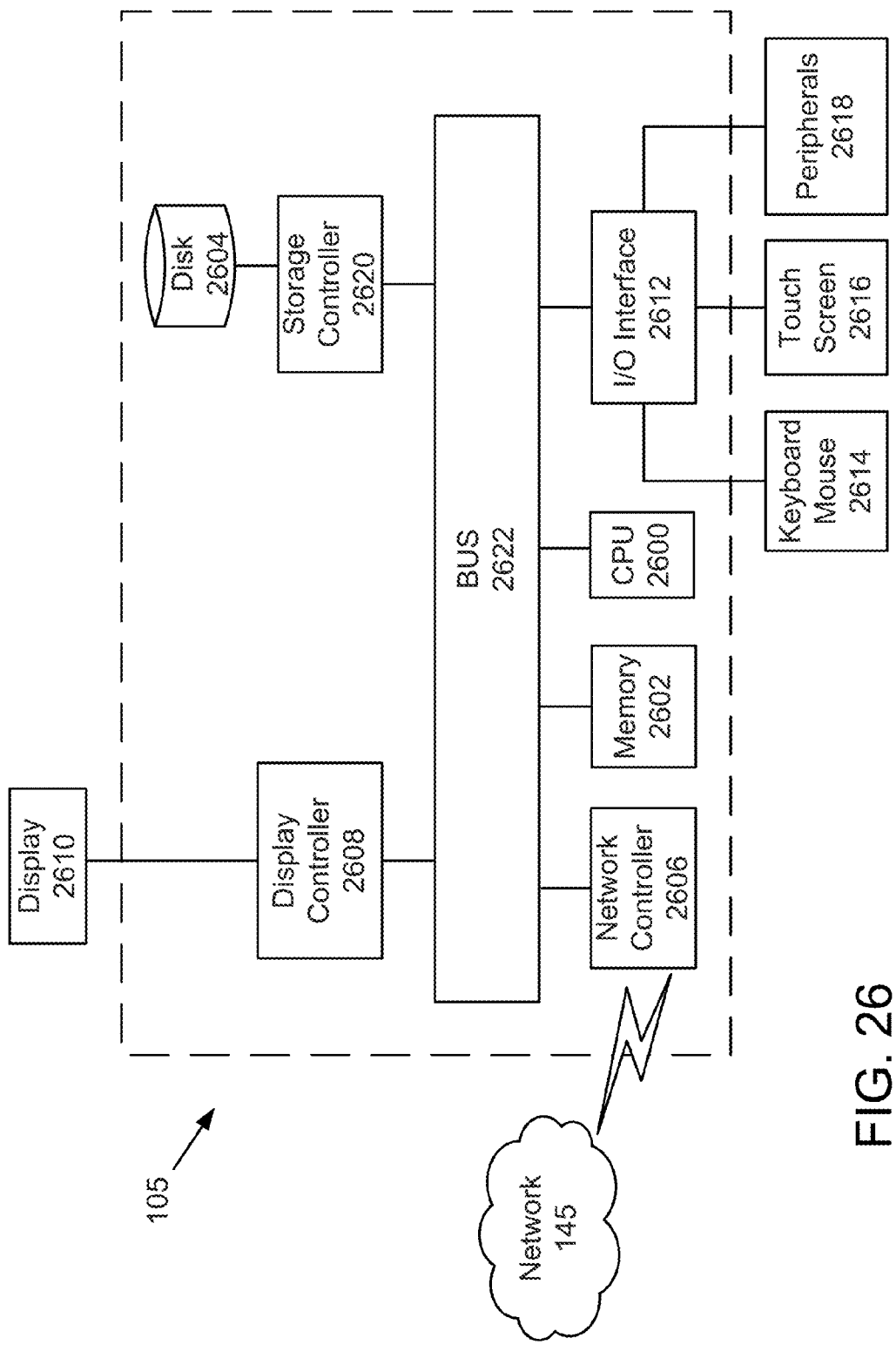
FIG. 26 is a schematic diagram of the controller of FIG. 1 according to certain embodiments of the disclosure.

FIG. 26 is a schematic diagram of the controller 105 of FIG. 1 according to certain embodiments of the disclosure. In FIG. 26, a hardware description of the controller 105 according to exemplary embodiments is described. In FIG. 26, the controller 105 includes a CPU 2600 which performs the processes described above/below. The process data and instructions may be stored in memory 2602. These processes and instructions may also be stored on a storage medium disk 2604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the controller 105 communicates, such as a server or computer.

Further, the claimed advancements may be provided as a utility application, background daemon, or component of an operating system, or combination thereof, executing in conjunction with CPU 2600 and an operating system such as Microsoft Windows®, UNIX®, Solaris®, LINUX®, Apple® MAC-OS and other systems known to those skilled in the art.

The hardware elements in order to achieve the controller 105 may be realized by various circuitry elements, known to those skilled in the art. For example, CPU 2600 may be a Xeon® or Core® processor from Intel® of America or an Opteron® processor from AMD® of America, or may be other processor types that would be recognized by one of ordinary skill in the art. Alternatively, the CPU 2600 may be implemented on an FPGA, ASIC, PLD or using discrete logic circuits, as one of ordinary skill in the art would recognize. Further, CPU 2600 may be implemented as multiple processors cooperatively working in parallel to perform the instructions of the inventive processes described above.

The controller 105 in FIG. 26 also includes a network controller 2606, such as an Intel® Ethernet PRO® network interface card from Intel® Corporation of America, for interfacing with network 145. As can be appreciated, the network 145 can be a public network, such as the Internet, or a private network such as an LAN or WAN network, or any combination thereof and can also include PSTN or ISDN sub-networks. The network 145 can also be wired, such as an Ethernet network, or can be wireless such as a cellular network including EDGE, 3G and 4G wireless cellular systems. The wireless network can also be WiFi, Bluetooth, or any other wireless form of communication that is known.

In certain embodiments, apparatus 100 may be controlled and operated remotely via network 145 by a user equipment, such as a smartphone, tablet computer, laptop computer or the like.

The controller 105 further includes a display controller 2608, such as a NVIDIA® GeForce GTX® or Quadro® graphics adaptor from NVIDIA® Corporation of America for interfacing with display 2610, such as a Hewlett Packard® HPL2445w LCD monitor. A general purpose I/O interface 2612 interfaces with a keyboard and/or mouse 2614 as well as a touch screen panel 2616 on or separate from display 2610. General purpose I/O interface also connects to a variety of peripherals 2618 including printers and scanners, such as an OfficeJet® or DeskJet® from Hewlett Packard®.

The general purpose storage controller 2620 connects the storage medium disk 2604 with communication bus 2622, which may be an ISA, EISA, VESA, PCI, or similar, for interconnecting all of the components of the controller 165. A description of the general features and functionality of the display 2610, keyboard and/or mouse 2614, as well as the display controller 2608, storage controller 2620, network controller 2606, and general purpose I/O interface 2612 is omitted herein for brevity as these features are known.

The above-described hardware description is a non-limiting example of corresponding structure for performing the functionality described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

ABBREVIATIONS $A_b$=Area of Anchor Bolt
D=Stress Reduction Ratio due to crack propagation/Stress Release
$E_b$=Elastic Modulus of Anchor
L=Bolt Embedment Length
$L_e$=Exposed Length
P*=Bolt Pull-out Force
P=Pull-out Strength Capacity
q=Shear Force per unit Length on Bolt
$q_f$=Frictional Shear Force per unit Length on de-bonded Bolt Interface
$q_y$=Yield Shear Force per unit Length
R=Rebound Value
$S_{end}$=End Constant Representing Anchor End Shape
U*=Bolt Pull-out Displacement
y=De-bonded Length of Interface owing to Impact Loading
F=Substitution
$\overline{\omega}$=Interface Parameter

The invention claimed is:

1. An apparatus for determining a pull-out capacity of a bolt disposed in concrete at an installation site, comprising:
   control processing circuitry coupled to a remote computer and a Global Positioning System (GPS) receiver;
   a Schmidt hammer electrically connected to the control processing circuitry, wherein the Schmidt hammer is configured to strike the bolt during a test event, wherein a rebound value for the bolt is recorded via a data acquisition system of the Schmidt hammer; and
   at least three location transmitters at the installation site, each said location transmitter being configured to wirelessly communicate with the control processing circuitry,
   wherein the control processing circuitry is configured to determine an estimated pull-out strength for the bolt using the rebound value of the bolt that resulted from the test event, and based on data in the form of a predetermined bolt diameter, a predetermined bolt embedment length in the concrete, and an estimated predetermined strength of concrete saved in a database, the data being correlated with a predetermined rebound value stored in the database,
   wherein the remote computer is configured to communicate with the control processing circuitry, and store an estimated pull-out strength of the bolt, wherein the control processing circuitry includes a memory and a database,
   wherein the Schmidt hammer is configured to record a predetermined location of the bolt being tested by using triangulation according to said at least three location transmitters at the installation site and a GPS coordinate from the GPS receiver electronically coupled to the control processing circuitry, and
   wherein each bolt tested is assigned a unique ID that is saved in association with the predetermined location of the bolt and the rebound value.

2. The apparatus according to claim 1, wherein the remote computer is configured to monitor an installation process in real time of each bolt, compare the estimated pull-out strength for the bolt with a predetermined criteria and provide a certification indication that indicates whether the bolt was properly installed and provide a certification report so corrective action may be taken if the bolt was installed incorrectly.

3. The apparatus according to claim 2, wherein the remote computer is configured to provide feedback to a compliance computer whether the bolt is estimated to have a required pull-out strength.

4. The apparatus according to claim 1, wherein the control processing circuitry calculates the estimated pull-out strength according to at least one of:
$y=0.0036x^2+0.3654x$ for a predetermined diameter bolt;
$y=-0.0038x^2+0.7608x$; and
$y=0.0144x^2-0.3823x$, where x is the rebound value and y is the estimated pull-out strength for the predetermined bolt diameter.

5. A non-destructive method for determining a pull-out capacity of a bolt disposed in concrete at an installation site, comprising:
impacting a Schmidt hammer on the bolt for a test event, wherein the Schmidt hammer is electronically coupled to control processing circuitry, the control processing circuitry being configured to wirelessly receive data from at least three location transmitters at the installation site;
recording in a computer memory a hammer rebound value from the Schmidt hammer;
calculating, via the control processing circuitry, an estimated pull-out strength for the bolt using the hammer rebound value of the bolt that resulted from the test event, a predetermined bolt diameter saved in a database of the computer memory, a predetermined bolt embedment length in the concrete saved in the database, and an estimated predetermined strength of concrete saved in the database, the predetermined bolt diameter, bolt length, and strength of concrete being correlated with a predetermined rebound value stored in the database;
comparing with circuitry the recorded rebound value with a stored value stored in the database that is an association of the hammer rebound value to pull-out strength so as to estimate a pull-out load carrying capacity of the bolt; and
recording, via the Schmidt hammer data acquisition system, a predetermined location of the bolt being tested by using triangulation according to said at least three location transmitters at the installation site and a GPS coordinate from the GPS receiver,
wherein each bolt tested is assigned a unique ID that is saved in association with the predetermined location of the bolt and the rebound value.

6. The method according to claim 5, wherein the bolt is an anchor bolt and the stored value association includes a compilation of previous tests of pull-out strength verses rebound numbers of anchors bolts.

7. The method according to claim 5, wherein the stored value includes the predetermined bolt embedment length in the concrete, the predetermined bolt diameter, the predetermined bolt vertical alignment in the concrete, and the estimated predetermined strength of concrete.

8. The method according to claim 5, wherein a difference between the hammer rebound value to the stored value indicates whether the bolt is installed at an improper angle and whether a contact surface between the bolt is less than a predetermined amount.

9. The method according to claim 8, wherein the improper angle is greater than 5 degrees from an angle perpendicular to the concrete.

10. The method according to claim 5, wherein a difference between the hammer rebound value to the stored value indicates whether the concrete has a suboptimal amount of aggregate near the interface with the bolt.

11. The method according to claim 10, wherein the control processing circuitry is further configured to
compare the estimated pull-out load carrying capacity to a predetermined stored value so as to determine whether the bolt satisfies a predetermined pull-out strength.

12. The method according to claim 10, wherein the Schmidt hammer, the plurality of location transmitters, the controller, and the remote computer are connected to a network.

13. The method according to claim 12, wherein the network is at least one of a cellular network, a WiFi network, and an Internet network.

14. The method according to claim 10, wherein the remote computer is configured to monitor an installation process in real time of the bolt and other bolts and provides feedback to a compliance computer whether the installed bolt is estimated to have the required pull-out load carrying capacity.

15. The method according to claim 10, wherein the remote computer is configured to monitor an installation process in real time of each bolt, compare the estimated pull-out strength for the bolt with a predetermined criteria and provide a certification indication that indicates whether the bolt was properly installed and provide a certification report so corrective action may be taken if the bolt was installed incorrectly.

16. The method according to claim 5, further comprising wirelessly transmitting the estimated pull-out load carrying capacity to a remote computer.

17. A system for determining a pull-out capacity of a bolt disposed in concrete at an installation site, comprising:
control processing circuitry;
a Schmidt hammer electrically connected to the control processing circuitry, wherein the Schmidt hammer is configured to strike the bolt during a test event and to record a rebound value for the bolt via a data acquisition system of the Schmidt hammer;
a remote computer configured to communicate with the control processing circuitry and to store an estimated pull-out strength of the bolt, wherein the control processing circuitry includes a memory and a database;
a global positioning system (GPS) receiver electrically connected to the control processing circuitry; and
at least three location transmitters at the installation site, each said location transmitter being configured to wirelessly communicate with the control processing circuitry,
wherein the remote computer is further configured to
record a predetermined location of the bolt being tested by using triangulation according to said at least three location transmitters at the installation site and a GPS coordinate from the GPS receiver electronically coupled to the control processing circuitry,
wherein each bolt tested is assigned a unique ID that is saved in association with the predetermined location of the bolt, the rebound value, and the estimated pull-out strength, and
wherein the control processing circuitry is configured to determine the estimated pull-out strength for the bolt using the rebound value of the bolt that resulted from the test event, and based on data in the form of a predetermined bolt diameter, a predetermined bolt embedment length in the concrete, and an estimated predetermined strength of concrete saved in a database, the data being correlated with a predetermined rebound value stored in the database.

18. The system according to claim 17, wherein the control processing circuitry calculates the estimated pull-out strength according to at least one of:

$y=0.0036x^2+0.3654x$ for a predetermined diameter bolt;
$y=-0.0038x^2+0.7608x$; and
$y=0.0144x^2-0.3823x$, where x is the rebound value and y is the estimated pull-out strength for the predetermined bolt diameter.

* * * * *